United States Patent
Kim et al.

(10) Patent No.: US 11,808,754 B2
(45) Date of Patent: *Nov. 7, 2023

(54) ULTRASOUND DEVICES AND SYSTEMS FOR DETERMINING CONSTITUTIVE RELATIONS AND FIBER ORIENTATION OF SOFT TISSUES

(71) Applicant: University of Pittsburgh—Of the Commonwealth System of Higher Education, Pittsburgh, PA (US)

(72) Inventors: Kang Kim, Pittsburgh, PA (US); Choon Hwai Yap, Singapore (SG)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 956 days.

This patent is subject to a terminal disclaimer.

(21) Appl. No.: 16/727,879

(22) Filed: Dec. 26, 2019

(65) Prior Publication Data

US 2020/0191766 A1 Jun. 18, 2020

Related U.S. Application Data

(62) Division of application No. 14/772,363, filed as application No. PCT/US2014/021278 on Mar. 6, 2014, now Pat. No. 10,564,143.

(60) Provisional application No. 61/773,736, filed on Mar. 6, 2013.

(51) Int. Cl.
G01N 33/483 (2006.01)
G01N 29/06 (2006.01)
G01N 29/44 (2006.01)

(52) U.S. Cl.
CPC ..... *G01N 33/4833* (2013.01); *G01N 29/0654* (2013.01); *G01N 29/4418* (2013.01); *G01N 2291/02475* (2013.01); *G01N 2291/02827* (2013.01)

(58) Field of Classification Search
None
See application file for complete search history.

(56) References Cited

U.S. PATENT DOCUMENTS

2007/0118033 A1 5/2007 Lee
2010/0191111 A1 7/2010 Azuma
2012/0243758 A1 9/2012 Otani et al.

OTHER PUBLICATIONS

Eilaghi et al., "Biaxial mechanical testing of human sclera," *Journal of Biomechanics* 43(9): 1696-1701, Jun. 2010.
Gundiah, et al., "Determination of strain energy function for arterial elastin: experiments using histology and mechanical tests," *Journal of Biomechanics* 40(3): 586-594, Jan. 2007 (Abstract Only).
Konofagou et al., "A new elastographic method for estimation and imaging of lateral displacements, lateral strains, corrected axial strains, and poisson's ratios in tissues," *Ultrasound in Medicine and Biology* 24(8): 1183-1199, Oct. 1998.
Pan, et al., "Ultrasonic and viscoelastic properties of skin under transverse mechanical stress in vitro," *Ultrasound in Medicine & Biology* 24(7):995-100, Sep. 1998 (Abstract Only).

*Primary Examiner* — G. Steven Vanni
(74) *Attorney, Agent, or Firm* — Klarquist Sparkman, LLP

(57) ABSTRACT

The systems and methods provided herein relate to the performance of inverse reconstruction algorithms from ultrasound radiofrequency data and stress-strain data. These systems and methods can be applied to any soft tissue mechanical measurements, providing information about both mechanical properties and fiber orientation, and the relationships between them.

8 Claims, 22 Drawing Sheets

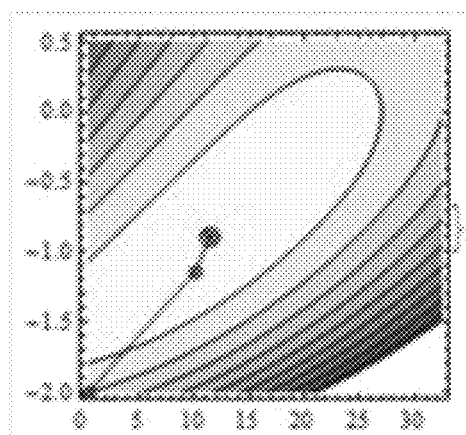
FIG. 6
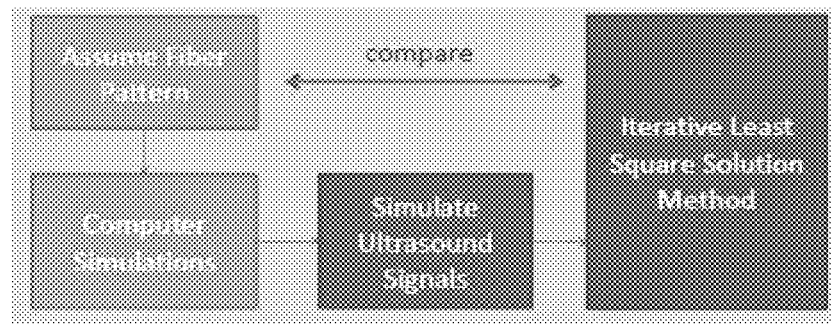
FIG. 7
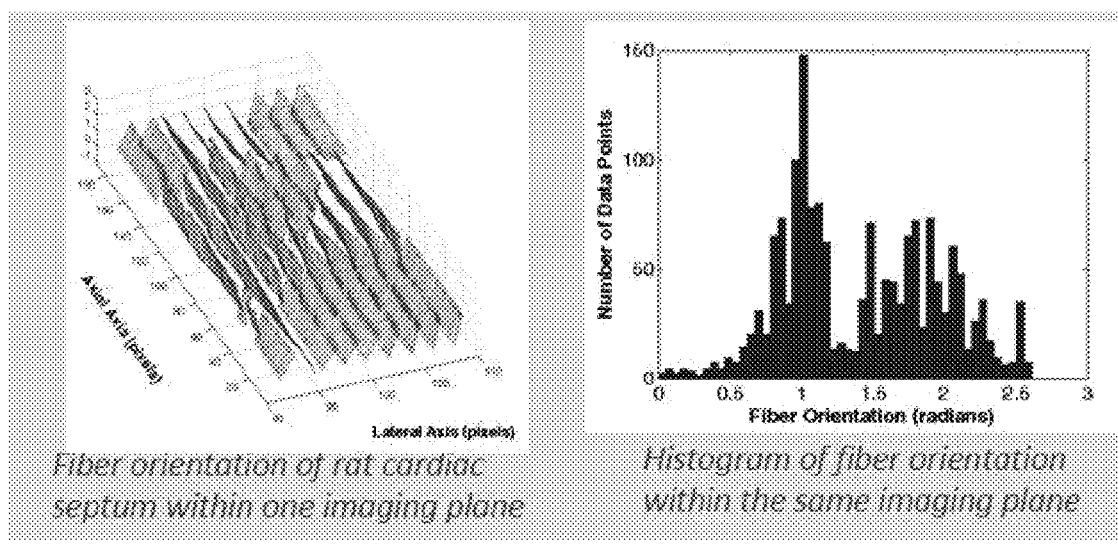
FIG. 8        FIG. 9

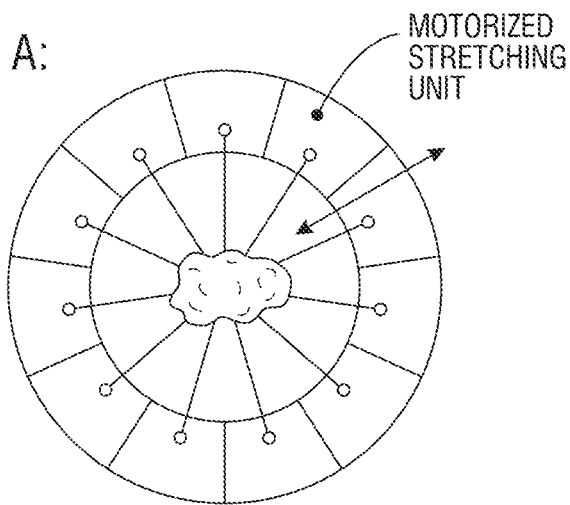
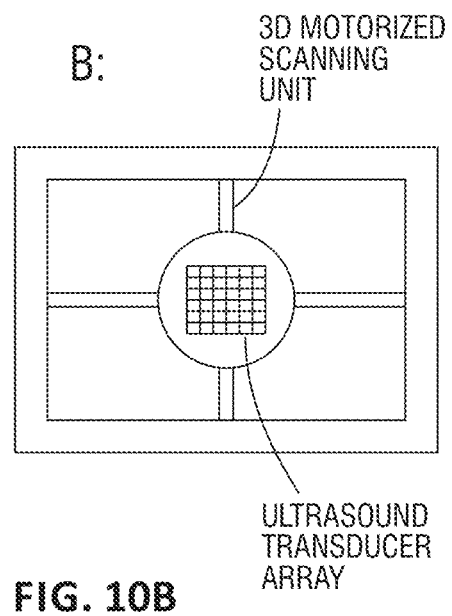
FIG. 10A  FIG. 10B
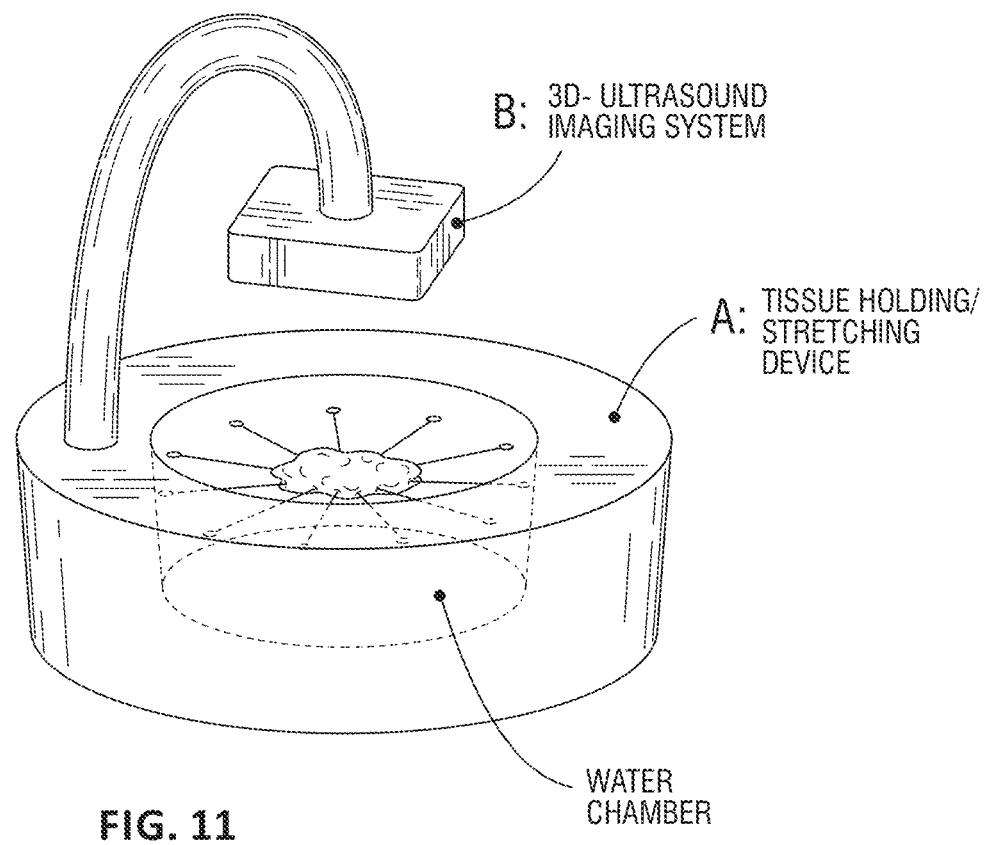
FIG. 11

| Actual Angle | Computed angle | Coefficient 1 | Coefficient 2 | Coefficient 3 | Coefficient 4 |
|---|---|---|---|---|---|
| 0.00 | -0.32 | 100.0 | 14.00 | 100.0 | 55.00 |
| 2.86 | 2.40 | 100.0 | 14.00 | 99.95 | 54.99 |
| 5.73 | 5.40 | 100.0 | 14.00 | 99.80 | 54.97 |
| 17.2 | 17.4 | 99.90 | 14.00 | 100.6 | 55.06 |
| 28.6 | 28.8 | 99.82 | 14.00 | 101.2 | 55.06 |
| 40.1 | 40.2 | 99.61 | 14.01 | 101.3 | 55.79 |
| 51.6 | 51.6 | 100.2 | 14.00 | 99.06 | 54.93 |
| 63.0 | 63.0 | 100.0 | 14.00 | 99.73 | 55.05 |
| 74.5 | 74.4 | 99.99 | 14.00 | 100.0 | 55.01 |
| 84.2 | 85.2 | 100.0 | 14.00 | 100.0 | 55.00 |
| 87.1 | 89.4 | 100.1 | 14.00 | 99.31 | 55.11 |
| 90.0 | 89.4 | 100.0 | 14.00 | 100.0 | 55.00 |
| Actual Coefficients for all cases: | | 100.0 | 14.00 | 100.0 | 55.00 |

FIG. 31

| Loading Condition Combinations | | b (Pa) | c | A (Pa) | a |
|---|---|---|---|---|---|
| Single Loading Condition | | | | | |
| $\sigma_L = \sigma_E$ | | 103.15 | 13.91 | 68.15 | 62.86 |
| $\sigma_L = 1.1\sigma_E$ | | 108.07 | 13.71 | 29.00 | 98.36 |
| Two Loading Conditions | | | | | |
| – higher load in Lateral axis for both conditions | | | | | |
| $\sigma_L = 1.05\sigma_E$; | $\sigma_L = 1.15\sigma_E$ | 99.94 | 14.00 | 102.65 | 54.31 |
| $\sigma_L = 1.1\sigma_E$; | $\sigma_L = 1.15\sigma_E$ | 103.10 | 13.90 | 66.80 | 64.35 |
| $\sigma_L = 1.1\sigma_E$; | $\sigma_L = 1.05\sigma_E$ | 105.13 | 13.81 | 45.05 | 82.42 |
| Two Loading Conditions | | | | | |
| – higher Lateral axis load for one, higher Elevational axis load for the other | | | | | |
| $\sigma_L = 1.05\sigma_E$; | $\sigma_E = 1.05\sigma_L$ | 99.53 | 14.01 | 105.74 | 53.91 |
| $\sigma_L = 1.1\sigma_E$; | $\sigma_E = 1.1\sigma_L$ | 100.64 | 13.99 | 104.17 | 52.19 |
| $\sigma_L = 1.15\sigma_E$; | $\sigma_E = 1.15\sigma_L$ | 99.04 | 14.034 | 118.17 | 50.40 |
| Three Loading Conditions | | | | | |
| $\sigma_L = \sigma_E$; | $\sigma_L = 1.1\sigma_E$; $\sigma_E = 1.1\sigma_L$ | 100.74 | 13.98 | 102.29 | 52.65 |
| Actual value of coefficients : | | 100.00 | 14.00 | 100.00 | 55.00 |

FIG. 32

|  | 1st SEF (Eqn.1) Loading condition 1 | | 1st SEF (Eqn.1) Loading condition 2 | | 2nd SEF (Eqn.3) Loading condition 1 | | 2nd SEF (Eqn.3) Loading condition 2 | |
|---|---|---|---|---|---|---|---|---|
|  | Lat. axis | Elev. axis | Lat. axis | Elev. axis | Lat. axis | Elev. axis | Lat. axis | Elev. axis |
| $M_1^q$ (kPa) | 4.84 | 10.00 | 4.45 | 6.91 | 4.76 | 9.48 | 4.09 | 6.24 |
| $\dfrac{M_1^q}{\sigma_{11}^{mea}}$ | 0.686 | 1.26 | 0.685 | 0.424 | 0.669 | 1.15 | 0.624 | 1.56 |
| $A^q$ (kPa) | 0.45 | 0.57 | 0.21 | 0.98 | 0.30 | 0.42 | 0.16 | 0.73 |

FIG. 33

| Strain Energy Function Coefficients | (kPa) |
|---|---|
| b (kPa) | 0.7557 ± 0.116 |
| c | 3.585 ± 0.405 |
| A (kPa) | 1.436 ± 0.179 |
| a | 48.10 ± 1.19 |

FIG. 34

ULTRASOUND DEVICES AND SYSTEMS FOR DETERMINING CONSTITUTIVE RELATIONS AND FIBER ORIENTATION OF SOFT TISSUES

CROSS REFERENCE TO RELATED APPLICATIONS

This application is a divisional of U.S. patent application Ser. No. 14/772,363, filed Sep. 2, 2015, which is the U.S. National Stage of International Application No. PCT/US2014/021278, filed Mar. 6, 2014, which was published in English under PCT Article 21(2), which in turn claims the benefit of U.S. Provisional Patent Application No. 61/773,736, filed Mar. 6, 2013. The prior applications are incorporated herein by reference in their entirety.

FIELD

The systems and methods disclosed herein relate to techniques for identifying properties of complex tissue, including, for example, a fiber orientation of biological tissue.

BACKGROUND

Biological tissues such as myocardium and major arterial walls are complex structures, with multi-layered and anisotropic properties in the presence of load-bearing fibers. Knowledge of their mechanical structural behavior can provide a better understanding of tissue function. However, conventional techniques for obtaining fiber orientation of biological tissues, such as diffusion tensor magnetic resonance imaging, two-photon microscopy and small angle light scattering, have numerous deficiencies. For example, these methods do not measure the mechanical property of the tissues. In addition, the method of two-photon microscopy cannot be applied to thick optically opaque tissues unless drastic treatment such as decelluralization is performed, and the method of small angle light scattering only works on thin membranous tissues. Also, some of these technologies, like diffusion tensor magnetic resonance methods, require large and expensive equipment

SUMMARY

The systems and methods described herein can provide simultaneous measurements of tissue mechanical properties (e.g., constitutive relations) and spatially-varying fiber orientation for optically opaque biological sample with complex fiber orientations.

In one embodiment, a method for obtaining spatially-varying fiber orientation of an optically opaque sample is provided. The method can include stretching the sample along a plurality of axes, obtaining 3D ultrasound images of the stretched sample along the plurality of axes to determine an amount of strain on the sample, and determining a fiber orientation of the sample based, at least in part, on the determined amount of strain on the sample while stretched along the plurality of axes.

In some embodiments, the act of computing of the fiber orientation can include includes performing an inverse reconstruction algorithm using strain data obtained from the ultrasound images and stress data from a biaxial tester that stretches the sample. The acts of stretching the sample and obtaining ultrasound images can include increasing an amount that the sample is stretched over a number of stretch cycles and subsequently imaging the sample. The act of obtaining ultrasound images can include imaging the sample at a peak stretch amount of the respective cycle. The ultrasound images comprise ultrasound speckle images.

In other embodiments, the act of computing the fiber orientation can include generating a 3D strain data over a volume in the sample from the ultrasound speckle images, determining a stress data using a biaxial force measurement device while the sample is stretched along the plurality of axes, and computing the fiber orientation of the sample through non-linear curve fitting of the strain and stress data. The computing of the fiber orientation can include performing an iterative loop to match computed and measured stress data. The act of stretching the sample can include securing the sample at a plurality of locations along the edge of the sample and applying a stretching force to the sample. The stretching force can include a compressive force in the axial direction.

In other embodiments, a system for determining fiber orientation of tissue samples is provided. The system can include a biaxial tester configured to apply a force to a sample and an ultrasound device coupled to the biaxial tester and configured to move relative to the tissue sample. The biaxial tester can include a tissue holding device that is moveable via a motorized unit to vary the amount of force applied to the sample, and the ultrasound device can include a high-frequency 3D ultrasound speckle tracking device.

In some embodiments, the ultrasound device can be coupled to the biaxial tester and suspended over a sample-receiving area of the biaxial tester. The biaxial tester can include a plurality of sample-securing members (e.g., hooks, clips, clamps or the like) located around a sample-receiving area to secure the sample at a plurality of locations. The biaxial tester can include a plurality of pulleys to distribute a load applied to the sample. The biaxial tester can be configured to apply a periodically increasing load to the sample, and the ultrasound device can be configured to image the sample at a substantially peak stretch amount during each period.

In another embodiment, a method for determining fiber orientation of a tissue sample is provided. The method can include positioning the tissue sample in a sample-receiving area, securing the tissue sample at a plurality of locations around the tissue sample, applying forces to the sample at the plurality of locations to stretch the tissue sample to a first stretch amount, calculating an amount of stress on the tissue sample at the first stretch amount, imaging the tissue sample with an ultrasound device and obtaining a plurality of first ultrasound images of the tissue sample while at the first stretch amount, calculating an amount of 3D strain over the volume in the tissue sample at the first stretch amount, increasing the forces applied to the tissue sample at the plurality of locations to stretch the tissue sample to a second stretch amount, calculating an amount of stress on the tissue sample at the second stretch amount, imaging the tissue sample with an ultrasound device and obtaining a plurality of ultrasound images of the tissue sample while at the second stretch amount, calculating an amount of 3D strain over the volume in the tissue sample at the second stretch amount, and identifying a fiber orientation of the tissue sample based on the calculated amounts of stress and strain at the first and second stretch amounts.

In some embodiments, the act of applying forces to the sample can include uniformly stretching the tissue sample along a lateral axis and an elevational axis. The method can include the step of removing the applied forces from the sample to allow the tissue sample to return to a stress-free condition before increasing the forces applied to the tissue sample. The ultrasound images can include speckle tracking images.

The foregoing and other objects, features, and advantages of the invention will become more apparent from the following detailed description, which proceeds with reference to the accompanying figures.

BRIEF DESCRIPTION OF THE DRAWINGS

FIG. 6 illustrates iterative curve fitting between computed stress tensor and measured stress tensor.

FIG. 7 illustrates a schematic chart indicating an iterative approach to obtaining fiber orientation.

FIG. 8 illustrates fiber orientation of a rat cardiac septum within one imaging plane.

FIG. 9 illustrates a histogram of fiber orientation within the same imaging plane. The constitutive model output from the computation was as follows:

FIGS. 10A and 10B illustrate a biaxial testing apparatus and an imaging device, respectively.

FIG. 11 illustrates a testing device for determining a fiber orientation of a tissue sample using the devices shown in FIGS. 10A and 10B.

FIG. 31 illustrates results of an inverse computing of the SEFs and fiber orientation from the displacement data output from finite element simulations of the homogeneous fiber orientation cases.

FIG. 32 illustrates results of inverse computing the SEF from displacement data output from the finite element simulations of the first non-homogeneous fiber orientation case, where fiber angles vary with lateral coordinates FIG. 33 illustrates a goodness of fit between stress tensor diagonals measured from experiments and computed using the inverse algorithm, showing that fit can be improved by altering the SEF form.

FIG. 34 illustrates results of the inverse computation of the SEFs from the experimental speckle tracking data. The inverse computation was performed for both SEFs.

DETAILED DESCRIPTION

Figure 1A:
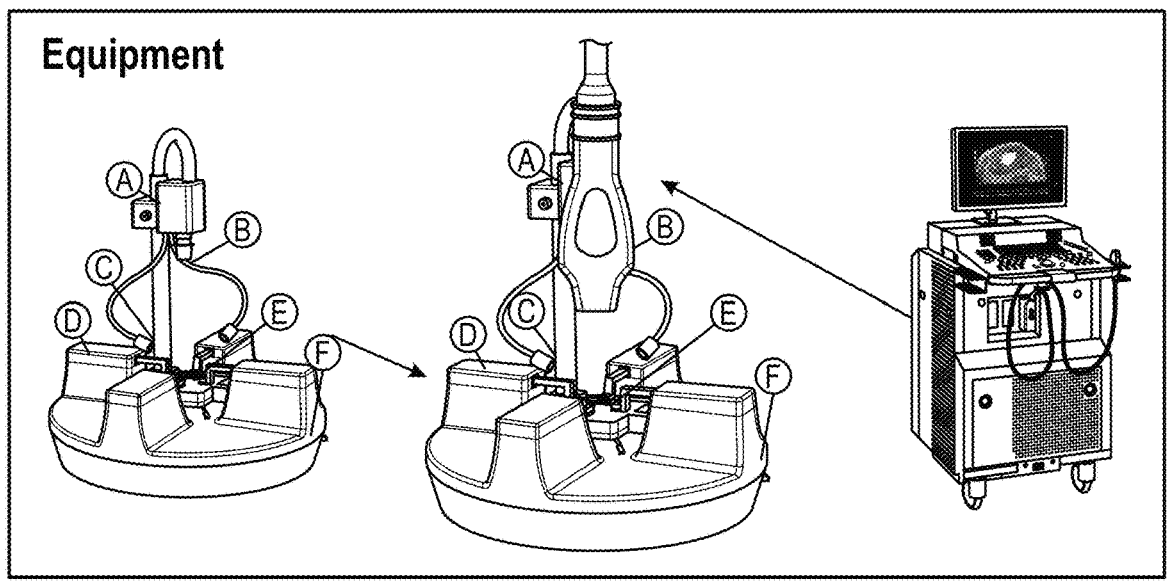
FIG. 1A illustrates equipment for using a schematic method for obtaining a fiber orientation of a tissue sample.
Figure 1B:
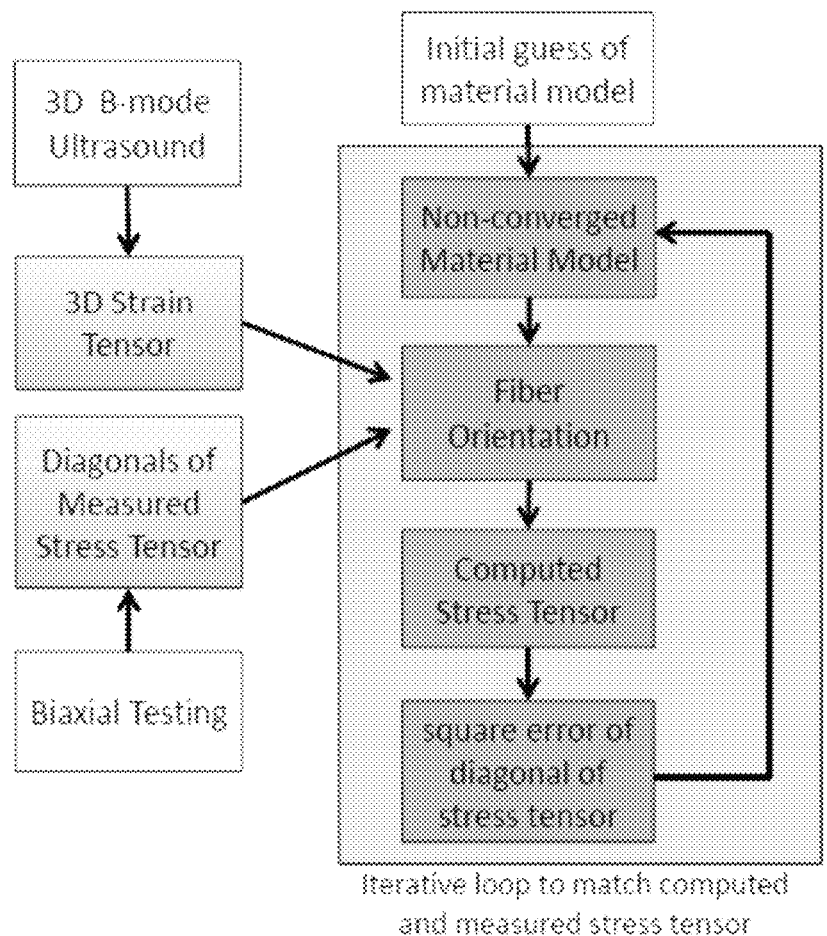
FIG. 1B illustrates a schematic method for obtaining a fiber orientation of a tissue sample, using a procedure to reconstruct constitutive relations and fiber orientations.

For purposes of this description, certain aspects, advantages, and novel features of the embodiments of this disclosure are described herein. The disclosed methods, apparatuses, and systems should not be construed as limiting in any way. Instead, the present disclosure is directed toward all novel and non-obvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed methods are described in a particular, sequential order for convenient presentation, it should be understood that this manner of description encompasses re-arrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "determine" and "provide" to describe the disclosed methods. These tetras are high-level abstractions of the actual operations that are performed. The actual operations that correspond to these terms may vary depending on the particular implementation and are readily discernible by one of ordinary skill in the art.

Biological tissues such as cardiac and arterial walls are structurally complex, being multi-layered and anisotropic, making it challenging to fully assess and understand their mechanical behavior. The systems and methods described herein provide deformation data below the surface to provide more information about tissue deformations. For example, as described in some embodiments below, mechanical testing can be combined with 3D ultrasound speckle tracking (3D-UST) to provide information about spatially-varying fiber orientation in addition to mechanical properties throughout the tissue thickness. In certain examples, high frequency ultrasound systems were used and samples were scanned in 3D while testing those samples with a biaxial tester. 3D-UST can generate the 3D strain tensor over a volume in the sample, while the diagonals of the stress tensor can be computed from biaxial force measurements. The strain-energy function (SEF) and fiber orientations can be computed through non-linear curve fitting of the stress and strain data. Finite element (FE) simulations can be used to validate the inverse computation algorithm, and histology can be used to support experimentally measured fiber orientations. As discussed in more detail below, FE-based simulations illustrate the effectiveness of this computing fiber orientations and SEF using the methods disclosed herein.

In some embodiments, the methods and systems described herein illustrate compact, simple, and relatively inexpensive devices that can be used to obtain both the mechanical properties (constitute relations) and the spatially varying fiber orientation over 3D volumes of tissues. Using these techniques, even thick, optically opaque volumes of tissue can be analyzed without the use of decelluralization treatments.

As shown in FIG. 1A, the system can comprise 3D ultrasound imaging devices and tissue stretching devices. A biaxial tester can measure a force imposed onto a particular sample, while the 3D ultrasound device measures tissue deformation in the 3D volume. In one example, discussed below, trimmed samples were placed into a saline bath for concurrent 3D ultrasound imaging and biaxial testing. 3D strain tensors are derived from 3D-UST of ultrasound images, while diagonals of the stress tensor are computed by dividing measured force by cross sectional area. The SEF coefficients are then computed from stress and strain values using an iterative non-linear curve fitting algorithm that minimizes the difference in measured and computed stress tensor diagonals. Within each iteration, fiber orientations are computed based on the non-converged SEF, also by matching computed and measured stresses, such that the optimization process can also seek least-square solutions to the originally unknown fiber orientations. The system, in some embodiments, assume that stress is uniform over respective cross sections.

Example 1

Biaxial Stretching and Imaging Example

Figure 2:
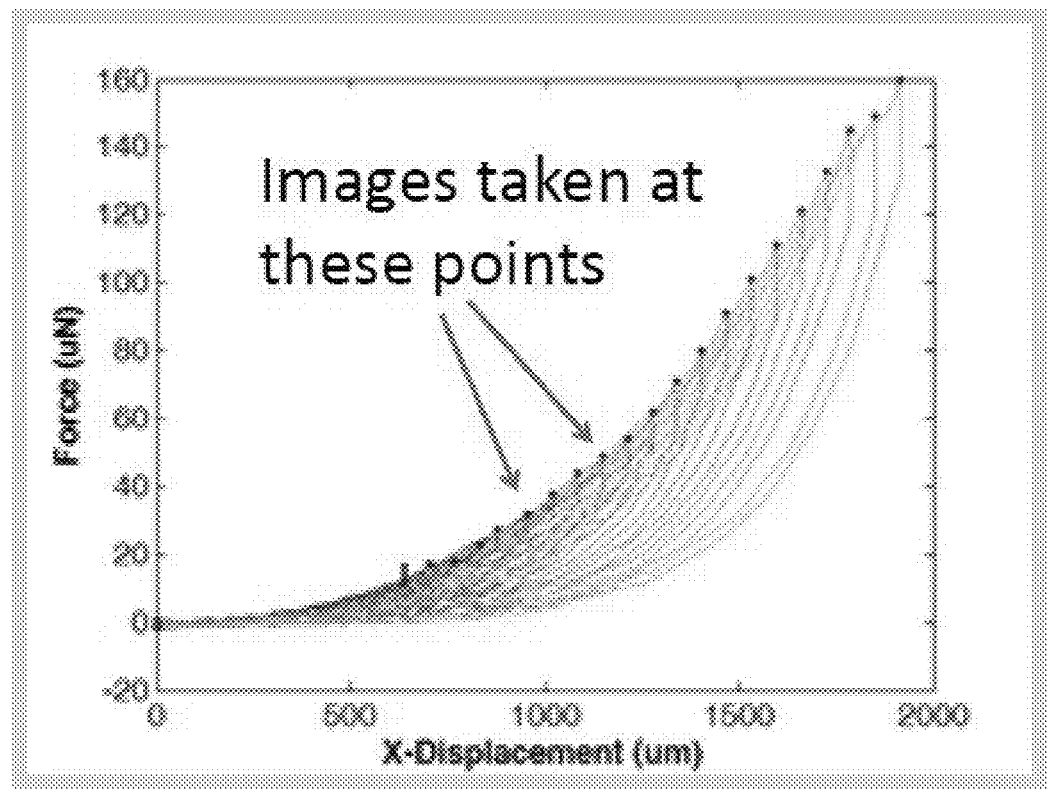
FIG. 2 illustrates a graph of x-displacement relative to force, and indicates the points at which images were taken.
Figure 3:
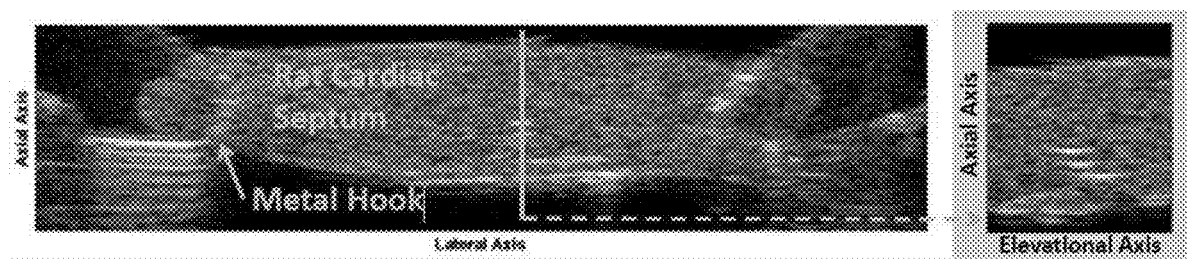
FIG. 3 shows images taken of a sample (e.g., rat cardiac septum along a lateral axis and an elevational axis).

A sample can be stretched periodically to a consecutively higher stretch amount. 3D ultrasound imaging can be performed at a peak stretch of each cycle, with the sample (e.g., tissue) held stationary for a predetermined amount of time (e.g., 5 seconds). Imaging was performed by a 30 MHz transducer (Vevo 2100, Visual Sonics, Canada), and the 3D volume was composed of 34-39 B-mode slices spaced by 0.1 mm. FIG. 2 illustrates a graph of x-displacement relative to force, and indicates the points at which images were taken. FIG. 3 shows images taken of a sample (e.g., rat cardiac septum along a lateral axis and an elevational axis).

3D Speckle Tracking and Strain Computation

Cross-correlation of the ultrasound speckle images were performed to compute displacements. Strains were computed as:

$$\varepsilon = \frac{1}{2}(F^T F - I)$$

where $F = \frac{du}{dx} + I$ $u$: displacement $x$: Eulerian coordinates

Figure 4:
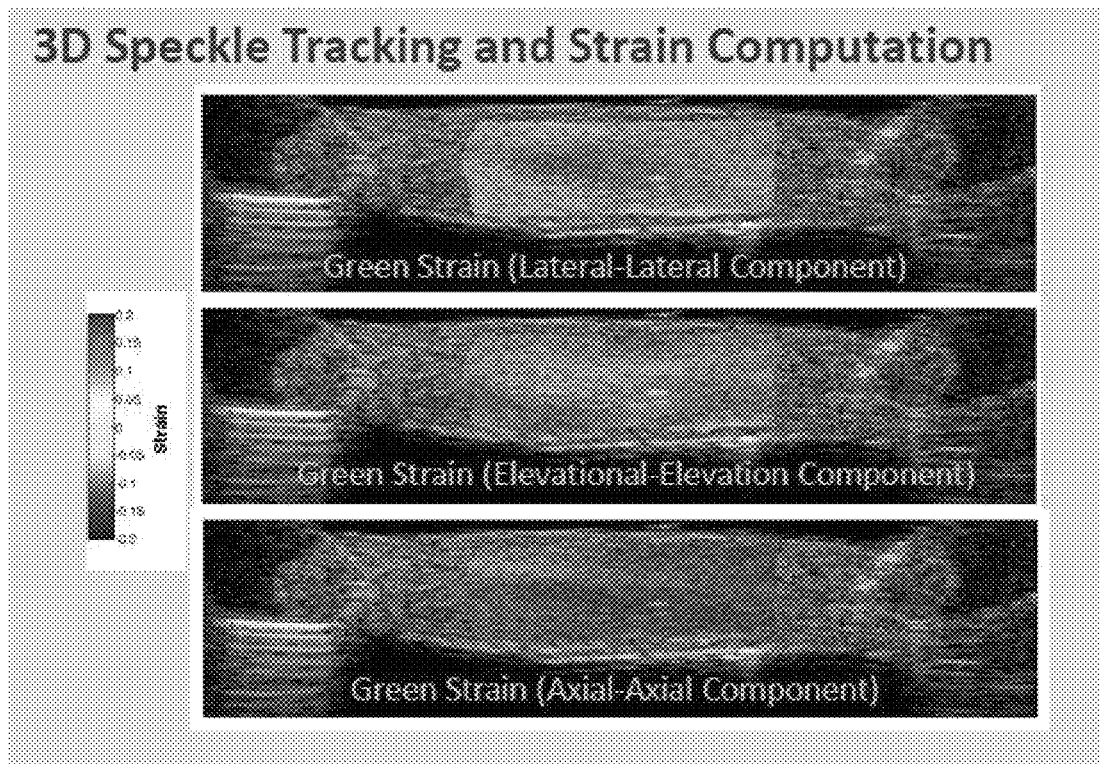
FIG. 4 shows 3D speckle tracking and strain computation along various components (e.g., lateral-lateral, elevation-elevation, and axial-axial).

FIG. 4 shows 3D speckle tracking and strain computation along various components (e.g., lateral-lateral, elevation-elevation, and axial-axial).

Tissue Material Model

Constitutive relations were calculated using the Humphrey model for myocardium, as set forth below:

$$\text{Cauchy Stress}(\sigma): \sigma = -pI + 2F\left(\frac{dW}{dC}\right)F^T$$

Figure 5:
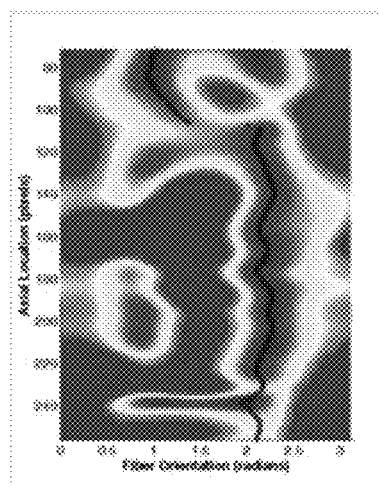
FIG. 5 illustrates an image showing determined fiber orientation. The color bar indicates error in computed stress and the black line indicates fiber orientation as a function of axial distance.

Strain Energy Function ($W$): $W(I_1, a) =$ $$W(I_1) + W_f(a) = c[e^{b(I_1-3)} - 1] + A\left[e^{a(a-1)^2} - 1\right]$$

Where $I_1 = tr(C)$; $a^2 = I_4 = N.C.N$ $p$: Lagrangian multiplier $F$: Deformational Gradient Tensor $C$: Left Cauchy-Green tensor $I_1$: 1$^{st}$ Strain Invariant $I_4$: 4$^{st}$ Strain Invariant $N$: Fiber Orientation vector Computation of Fiber Orientation At all locations, squared error of stress tensors diagonals were computed for all possible fiber orientations. Error was minimized using a path of minimal square error computation. As shown in FIG. 5, the color bar indicates error in computed stress and the black line indicates fiber orientation as a function of axial distance. As shown in FIG. 6, a trust region reflective algorithm was employed for iterative curve fitting between computed stress tensor and measured stress tensor.

Finite Element Simulations can be performed (e.g., using COMSOL®) to emulate the biaxial testing. In some embodiments, a specific Humphrey Strain Energy Function and fixed fiber orientation can be assumed for this step. The simulation output can be converted into ultrasound images as input into an algorithm to recover material model and fiber orientation. A schematic chart indicating these steps is provided in FIG. 7.

Reconstruction of Fiber Orientation and Strain Energy Function

FIG. 8 illustrates fiber orientation of a rat cardiac septum within one imaging plane and FIG. 9 illustrates a histogram of fiber orientation within the same imaging plane. The constitutive model output from the computation was as follows:

$$W = 0.650[e^{4.7(I_1-3)} - 1] + 8.23[e^{4.2(a-1)^2} - 1] \text{ kPa}$$

As shown below, the methods described herein provided similar results from that provided by FEM simulation.

|  | Simulation 1 | Recovered by our Method | Simulation 2 | Recovered by our method |
|---|---|---|---|---|
| Fiber Angle | Pi/4 | Pi/4 exactly | 1.0472 | 1.0053 |
| Model coeff1 | 100 | 98.8126 | 100 | 97.9251 |
| Model coeff2 | 14 | 14.0134 | 14 | 14.0467 |
| Model coeff3 | 100 | 96.7501 | 100 | 111.9114 |
| Model coeff4 | 55 | 60.9459 | 55 | 55.8319 |

Exemplary Systems for Performing the Methods Disclosed Herein

Figure 12:
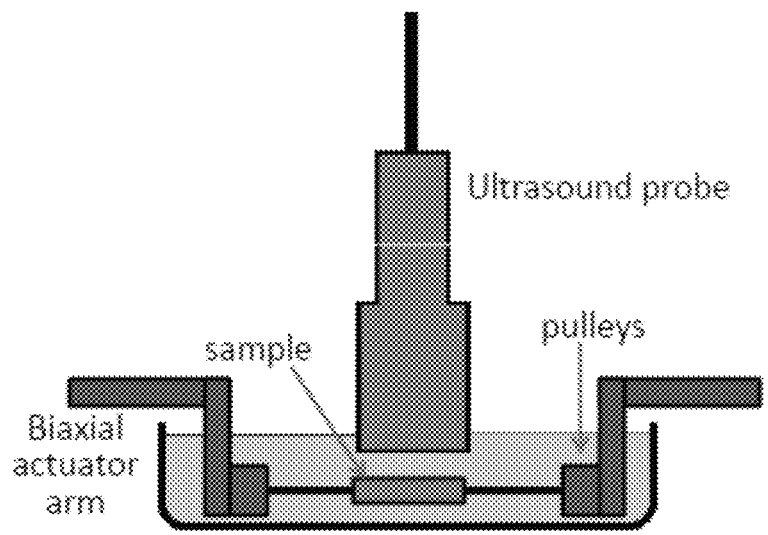
FIG. 12 illustrates an exemplary schematic of a biaxial tester and ultrasound imaging system.

FIG. 10A illustrates an exemplary motorized stretching unit for receiving and stretching tissue and FIG. 10B illustrates an exemplary 3D motorized scanning unit with an ultrasound transducer array that can be used in combination with the stretching unit. FIG. 11 illustrates a system with both a stretching unit and an imaging unit. As shown in FIG. 11, if desired, the sample that is to be stretched can be immersed in fluid, such as water during the stretching procedure. FIG. 12 illustrates another exemplary biaxial mechanical testing system with an ultrasound imaging device.

Example 2

Figure 13:
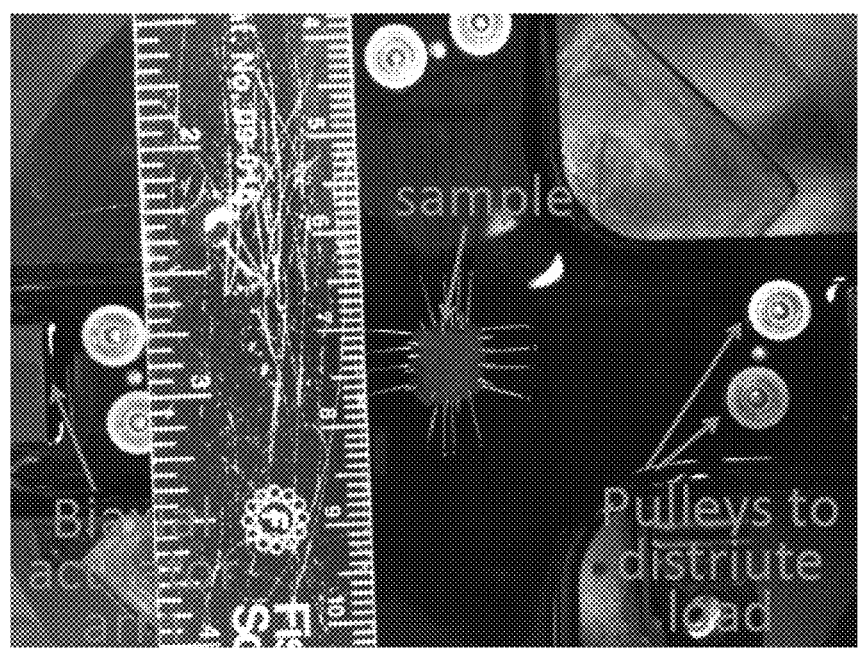
FIG. 13 illustrates an aerial view of a sample in a device of the type illustrated in FIG. 12.
Figure 14:
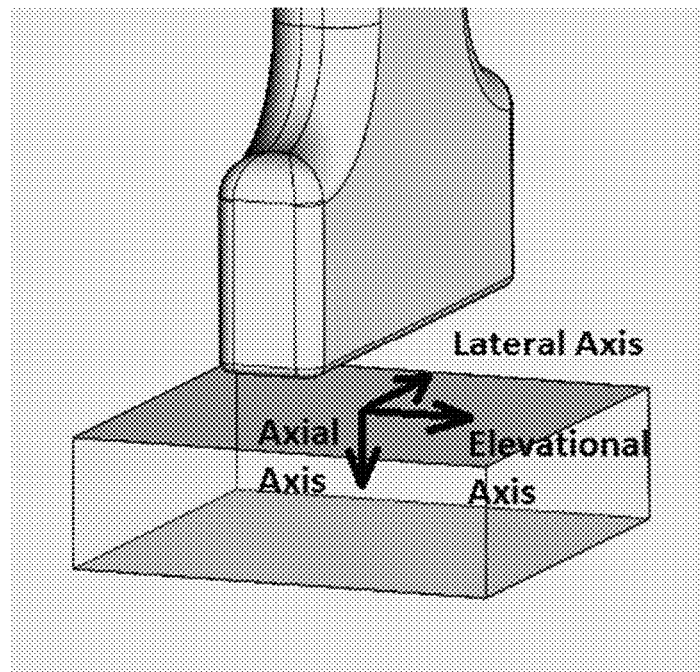
FIG. 14 illustrates a convention of axis coordinates.

Samples were tested with a commercial biaxial tester (BioTester, CellScale Inc., Waterloo, Ontario, Canada), and concurrent ultrasound imaging was performed using a 30 MHz linear array transducer (MS400, VisualSonics Inc., Canada) connected to a high frequency ultrasound system (Vevo2100, VisualSonics Inc., Canada), with the basic structure shown in FIG. 12. FIG. 13 illustrates an overhead plan view of the system, illustrating a biaxial actuator arm, pulleys to distribute load, and a sample subjected to biaxial loads. FIG. 14 illustrates the direction conventions discussed herein, including the axial, lateral, and elevational axes.

In this example, a rat left ventricular free wall sample was trimmed into a rectangular sample approximately 10 mm×10 mm in dimensions, and tested with the biaxial mechanical tester. A system of pulleys ensures the distribution of stresses along the edges of the sample. 3D ultrasound speckle images were gathered at each quasi-static stretch state by traversing a high frequency 2D linear-array transducer in the out-of-plane direction with a linear stepper motor, and scanning the sample at a regular spatial interval. Forces imposed on the sample were measured by force gauges attached to the biaxial actuator arms.

A small preload of 3 mN was applied to spread the sample out uniformly, and preconditioned was performed to the highest stretch level for 3 cycles. Due to the use of the linear actuator, each set of 3D ultrasound scan required approximately 4 seconds for the 39 slices of B-mode acquisition. A quasi-static biaxial testing protocol was adopted to accommodate this. The sample was stretched to consecutively higher stretch levels, and at each stretch level, the sample was held stationary for 6 seconds for ultrasound imaging. In between stretches, the sample was relaxed to the stress-free condition for 8 seconds.

Forces applied to the sample in the two stretch axes were measured with load cell and the diagonals of the stress tensor was computed through dividing by the cross sectional areas, which was measured from ultrasound images.

The ultrasound images were exported in the IQ modulated format. 3D-UST was applied to the reconstructed radiofrequency (RF) data to compute the spatially-varying three-component displacements over a volume in the sample. Green strains were then computed from displacements.

The SEF ($W$) for modeling the material property of the myocardium is provided by:

$$W = b(e^{c(I_1-3)^2} - 1) + a(e^{A(a-1)^2} - 1), \quad \text{(Eqn. 1)}$$

where b, c, A and a are the four coefficients defining the SEF, $I_1$ is the first invariant of the strain tensor, and α is the square-root of the forth invariant of the strain tensor. In the current implementation, it is assumed that the fiber orientations are only in the lateral-elevational plane (FIG. 14), and thus fibers can be described by a single angle parameter at every location. Alternatively, if additional computational time is not a concern, 3D fiber orientations can be modeled using two angle parameters instead of one.

The SEF coefficients were inversely-computed from the strain and stress tensors through an iterative non-linear curve fitting method that minimizes the sum-squared-error of the stress tensor diagonals:

$$\underset{SEF\ coefficients}{\mathrm{argmin}} \sum_{t \in \{lateral, elevational\}} \left( \sum_{x \in \{all\ points\}} \sigma_{ii}^{mea}(x) - \sum_{x \in \{all\ points\}} \sigma_{ii}^{comp}(x, SEF\ coefficients) \right)^2$$

(Eqn. 2), where $\sigma^{mea}_{ii}$ and $\sigma^{comp}_{ii}$ are the stress tensor diagonals along the ith axis: the former was measured from load cells, the latter computed by the curve fitting algorithm. The goodness of fit was evaluated with (1) the second moments ($M_2°$) of ($\sigma^{mea}_{ii} - \sigma^{comp}_{ii}$); and (2) absolute difference (A°) between mean values of $\sigma^{mea}_{ii}$ and mean values of $\sigma^{comp}_{ii}$.

In the curve-fitting above, the Trust Region Reflective algorithm was employed. All four SEF parameters were optimized at the same time, but upon completion of the curve-fitting, further optimization was performed to reduce the possibility that the solution was in a local minima instead of the global minima. A series of perturbation experiments and, within each experiment, one of the SEF coefficients was perturbed by doubling or halving its value, and the curve-fitting operation was repeated. Perturbation experiments were performed for all four SEF coefficients sequentially, for which the coefficient was doubled, and also where the coefficient was halved. If none of the perturbation experiments produced a lower residual than the initial curve-fitting, the initial result was assumed to have reached the global minima, otherwise the entire perturbation exercise was restarted with the new solution of lower residual. Fiber orientations were initially unknown, and were also recovered iteratively through the curve-fitting as well.

After the biaxial mechanical test, the same sample (rat LV) was fixed in formalin, and analyzed with standard Masson's Trichrome stain to obtain the actual fiber orientation. Stained slides were digitally scanned with Nikon Super Coolscan 9000 ED (Nikon, Melville, N.Y.) at a 6.3-micron pixel resolution, and analyzed with FFT using custom written Matlab® (Mathworks Inc., Natick, Mass.) programs at multiple points on the lateral-axial plane. Metal hooks were visible in the ultrasound images and holes made by hooks in the tissues were identified on the histological images. These were used as a landmark to geometrically register histology images to ultrasound images.

Figure 15A:
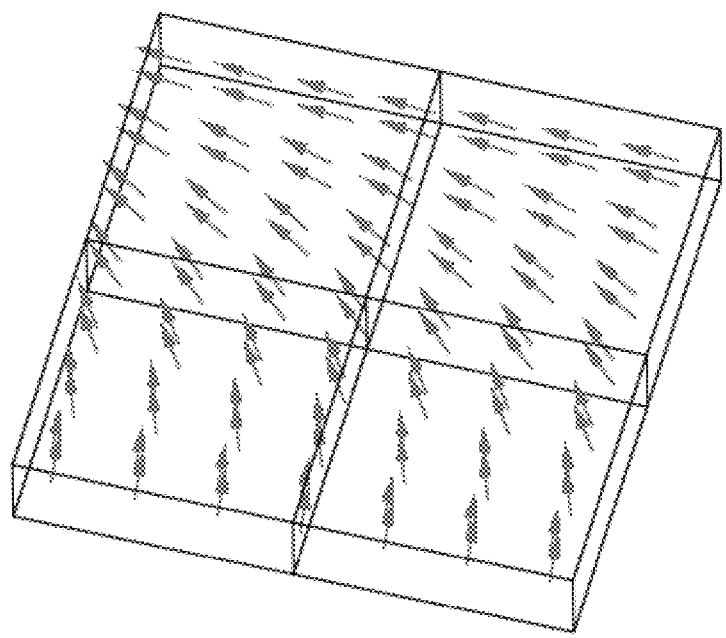
FIG. 15A illustrates a 3D model used in finite element simulations with arrows indicating the orientation of fibers at specific locations within the sample volume, with fiber orientations varying with the lateral axis.
Figure 15B:
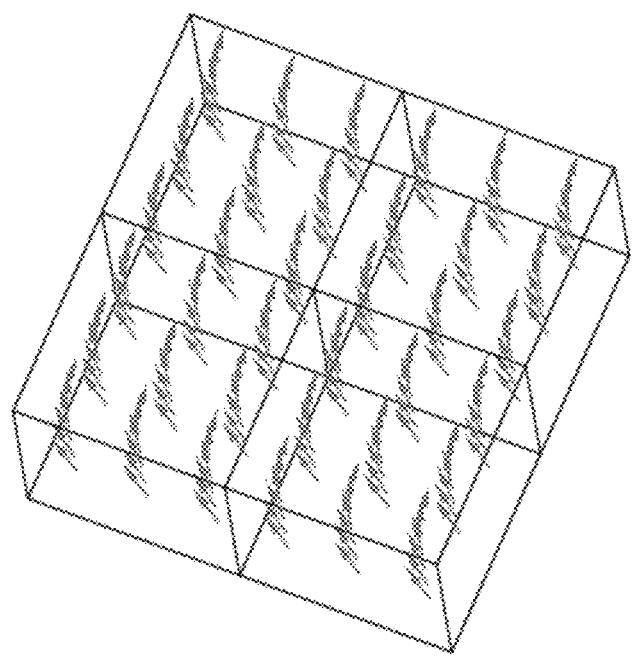
FIG. 15B illustrates a 3D model used in finite element simulations with arrows indicating the orientation of fibers at specific locations within the sample volume, with fiber orientations varying with the axial axis.

FEA of biaxial testing was performed. The resulting tissue displacements were analyzed with the inverse computation algorithm to examine the algorithm's ability to recover the original the fiber orientations and the SEF coefficients assumed by the simulation. FEA was performed using a commercial finite element simulation package (COMSOL®, Comsol Inc., Burlington, Mass.), and featured a rectangular tissue sample (dimensions: 30 mm×30 mm×3 mm or 30 mm×30 mm×10 mm in lateral, elevational, and axial axes) being stretched bi-axially with progressively greater uniform stress. 12 cases of homogeneous fiber orientations, with fiber angles ranging from 0 to 90 degrees (from the lateral axis) were simulated. Two cases of non-homogeneous fiber orientations were simulated: the first featured fiber orientation varying from 0 to 90 degrees along the lateral axis as shown in FIG. 15A; and the second featured fiber orientation varying from 0 to 57 degrees along the axial axis as shown in FIG. 15B.

FEA results showed that for tissues with homogeneous fiber angle, the inverse computation algorithm was highly accurate (table shown in FIG. 31), and that one set of loading condition was sufficient for the inverse computation. Slightly different loading in the two different loading axes was intentionally applied to reflect the fact that, during experiments, exactly similar stresses in these two axes cannot be practically achieved.

From the FEA, we found that the optimal loading condition for non-homogeneous fiber angle cases was where at least two sets of loading conditions were used, and where the two loading axis took turns to bear higher loads. This enhanced both accuracy and convergence (table shown in FIG. 32). FIG. 32 illustrates the results of inverse computing the SEF from displacement data output from the finite element simulations of the first non-homogeneous fiber orientation case, where fiber angles vary with lateral coordinates. Inverse computation was performed with a single set of loading condition at various magnitudes (with a fixed ratio of lateral versus elevational stress), or the combination of two or three sets of loading conditions. The results were more accurate when two sets of loading conditions were simultaneously analyzed using the inverse computation, instead of one. We further investigated cases where there are two loading conditions and both had higher stresses in one axis, as well as cases when there were two loading conditions, but each loading condition has a higher stress on a different axis. The later was found to converge easily, and to be the most accurate for the inverse computation. $\sigma_L$—stress in lateral direction; $\sigma_E$—stress in elevational direction. Convergence failure would sometimes result if only one loading condition was entered into the inverse computation. This was similarly observed during inverse computation with experimental data. This dual loading condition protocol was thus employed for all experiments in this study.

Figure 16A:
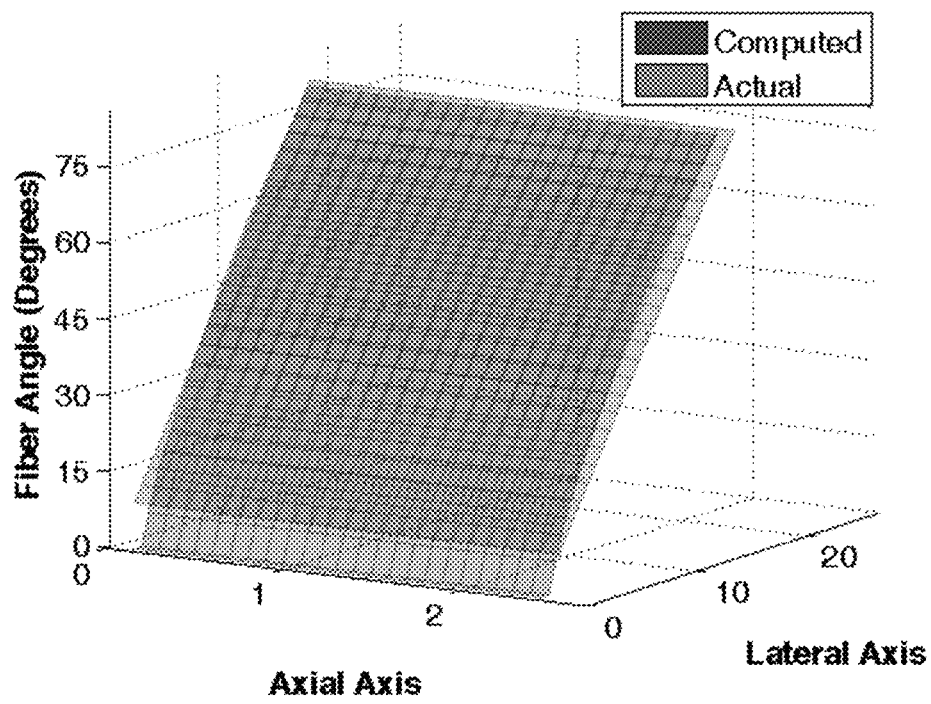
FIG. 16A illustrates fiber orientation computed by the non-linear curve fitting algorithm, using displacement data from finite element simulations as inputs, and of the truth fiber orientation used to perform the simulations, with results displayed for the finite element model where fiber angles vary with lateral axis.
Figure 16B:
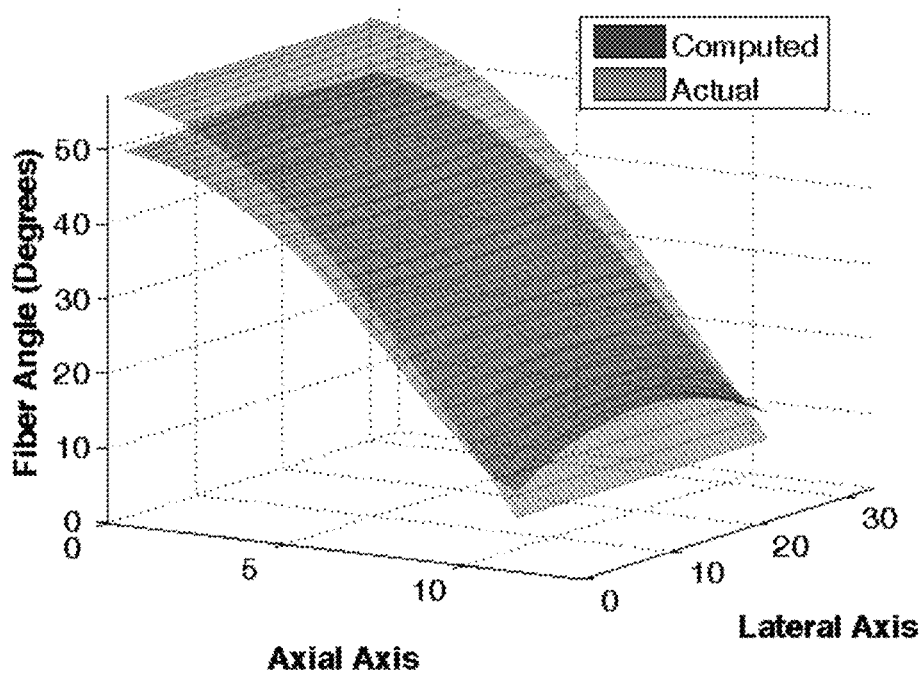
FIG. 16B illustrates fiber orientation computed by the non-linear curve fitting algorithm, using displacement data from finite element simulations as inputs, and of the truth fiber orientation used to perform the simulations, with results displayed for the finite element model where fiber angles vary with axial axis.

FIGS. 16A and 16B show the accuracy of the inverse computed fiber orientations for inhomogeneous fiber cases as well. From the first case in FIG. 16A, we noted that for fiber angles near to directions of loading (0 and 90 degrees), errors were consistently higher, but this was found to be a characteristic of the SEF used: when the SEF was switched to an alternative form, the problem ceased. In the second fiber pattern case (FIG. 16B), the errors that were encountered appear to greater non-uniformity in cross-sectional stresses.

In silico validation showed that the inverse computation algorithm could back-compute fiber angles and SEF highly accurately for FEA cases with homogeneous fiber angle as illustrated in the table shown in FIG. 31. Averaged over all 12 cases, errors in SEF were less than 0.3%, while errors in fiber orientation were less than 0.5 degrees.

The results for the cases with non-homogenous fiber orientation are summarized in the table shown in FIG. 32, and FIGS. 16A and 16B. It was found that, for samples with significantly inhomogeneous fiber orientation, at least two loading conditions were required for concurrent entry into the inverse computation algorithm in order for computation to be accurate, and for better solution convergence. As shown in the table shown in FIG. 32, for cases where only 1 loading conditions were entered, the $3^{rd}$ and $4^{th}$ SEF coefficients (a and A, respectively) can have large errors. With two loading conditions combined, if the loading conditions were always higher in one axis, results were not as accurate as if the higher loading alternated between the two axes. Accordingly, the latter method is generally preferred as a loading protocol. FIGS. 16A and 16B show the fiber orientation computed over one lateral-axial plane for the two inhomogeneous fiber orientation cases, showing a reasonable agreement between the back-computed and the actual fiber orientations.

Figure 17A:
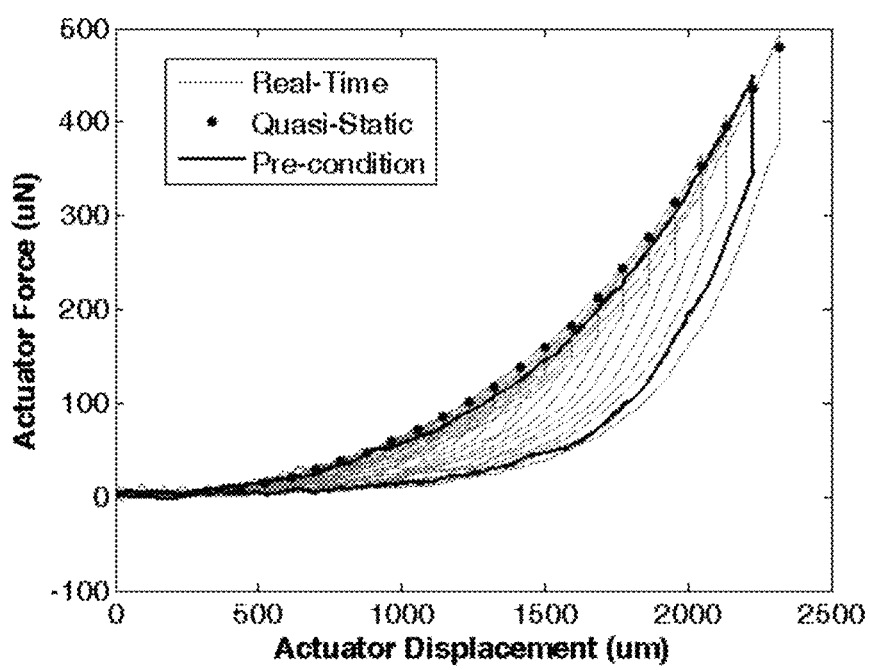
FIG. 17A illustrates a plot of real time force-displacement measurements from one biaxial actuator for preconditioning (black line) and actual testing (gray line), which imposed several stretch cycles to progressively higher quasi-static stretch levels.
Figure 17B:
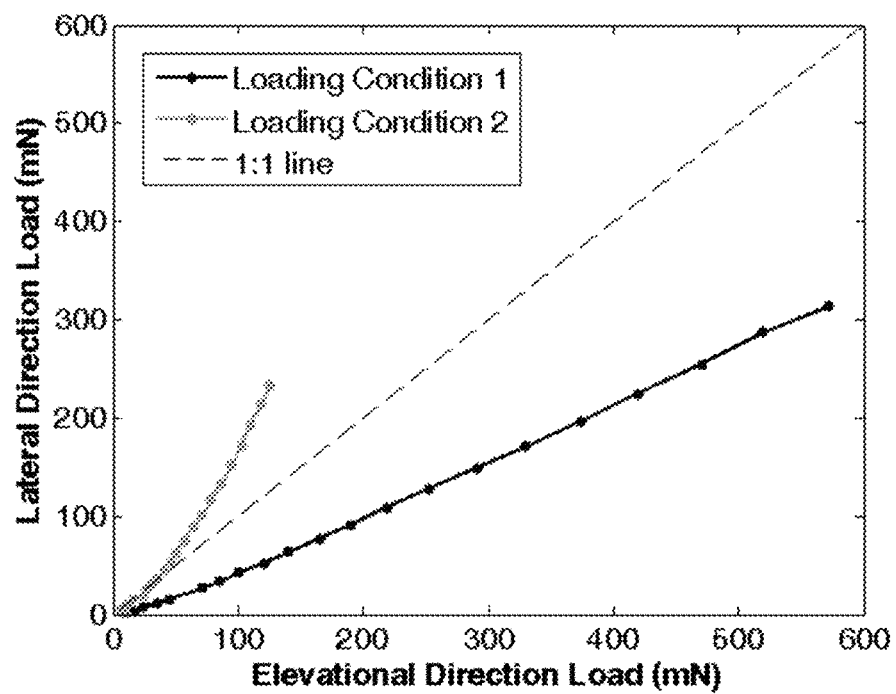
FIG. 17B illustrates plots of the two sets of loading conditions under which the sample was biaxially-tested.

FIG. 17A shows a typical real time force vs. displacement plot measured by the biaxial tester. The sample was tested with multiple loading cycles, each with a higher displacement and force than the previous. The rat left ventricular sample was tested under the two loading conditions protocol, as illustrated in FIG. 17B.

FIG. 17A illustrates a plot of real time force-displacement measurements from one biaxial actuator for preconditioning (black line) and actual testing (gray line), which imposed several stretch cycles to progressively higher quasi-static stretch levels. After each stretching phase, the sample was held stationary, and a set of ultrasound images was acquired. Each black dot represents the average of the first 5 data points after the beginning of this stationary phase, and is the force data assumed at each imaging point. The quasi-static manner of stretching (black dots) approximates the loading arm of a single stretch cycle, represented by the preconditioning cycle (black line), and is thus appropriate for use in modeling. FIG. 17B illustrates plots of the two sets of loading conditions under which the sample was biaxially-tested.

Figure 18:
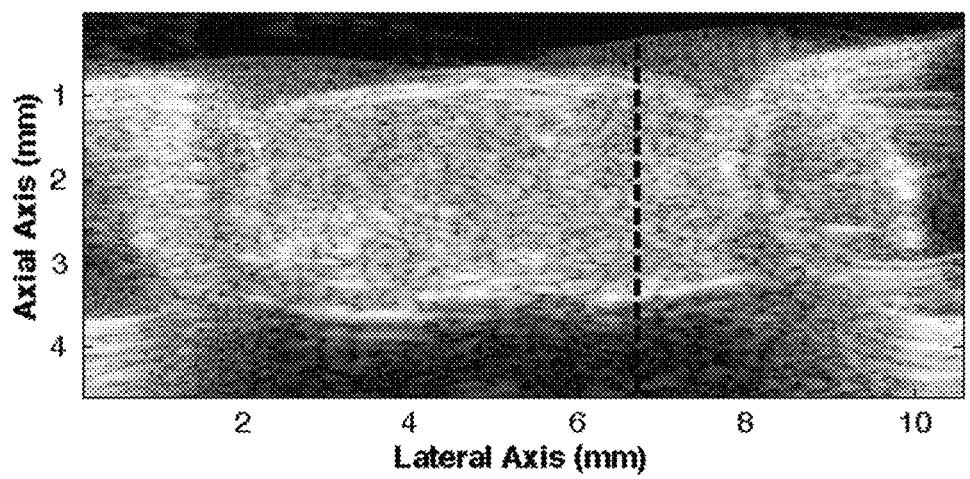
FIG. 18 illustrates representative Lateral-Axial plane raw ultrasound speckle image of the sample and the hooks attached to a sample.
Figure 19:
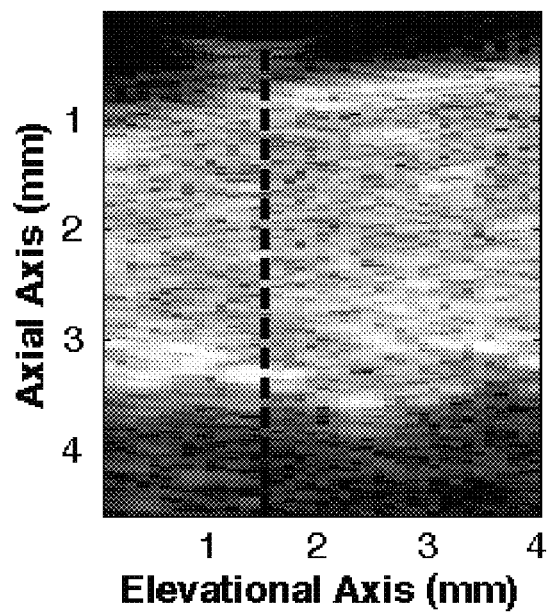
FIG. 19 illustrates representative Elevational-Axial plane raw ultrasound speckle image of a sample.

FIGS. 18 and 19 illustrate sample raw B-mode speckle images. FIG. 18 illustrates a representative Lateral-Axial plane raw ultrasound speckle image of the sample and the hooks attached to the sample. Thick dotted line indicates location for plotting FIG. 19. FIG. 19 illustrates a representative Elevational-Axial plane raw ultrasound speckle image of the sample. Thick dotted line indicates location for plotting FIG. 18.

Figure 20:
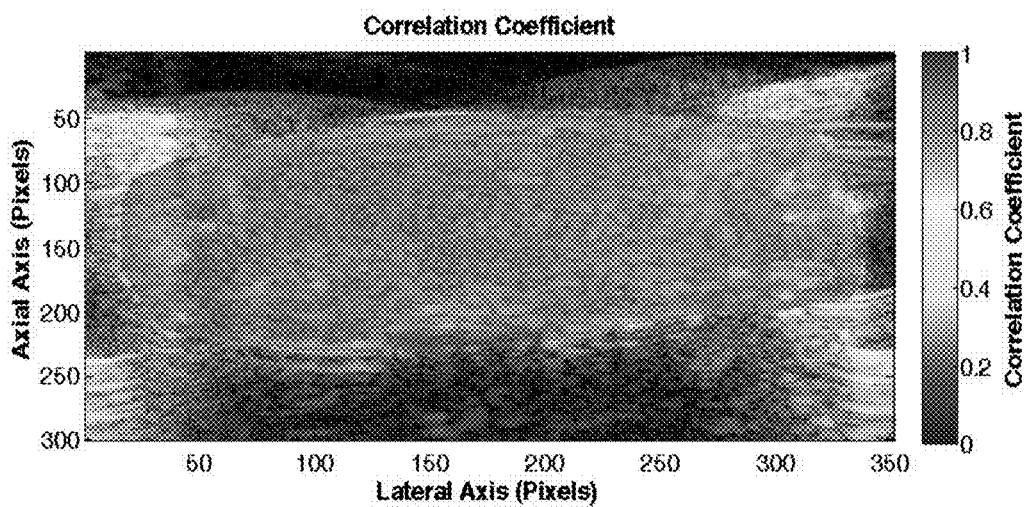
FIG. 20 illustrates a representative output from 3D speckle tracking moving from one stretch state to the next for correlation coefficient of the cross correlation pixel displacements between these two stretch states.
Figure 21:
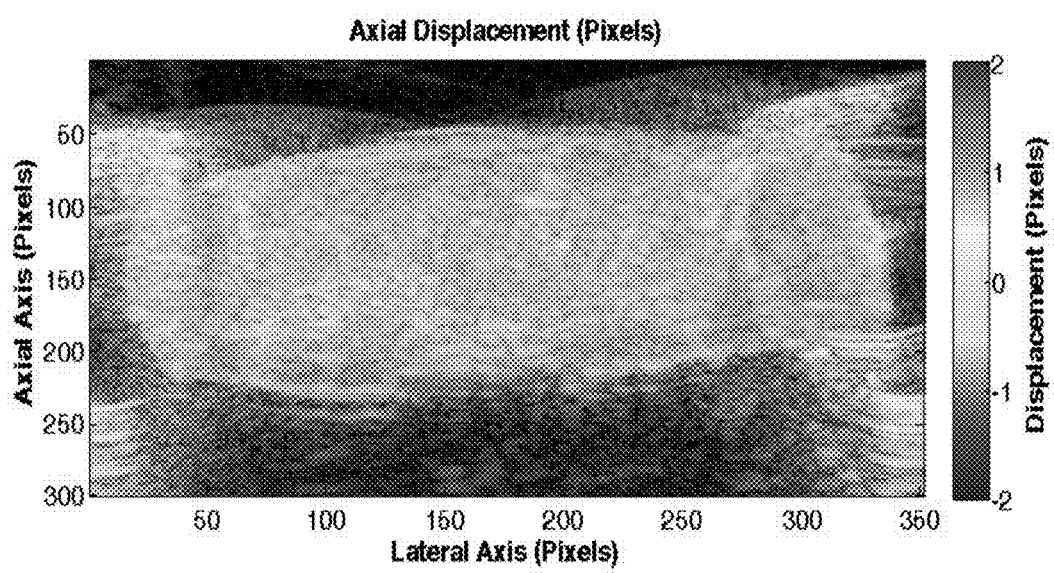
FIG. 21 illustrates a representative output from 3D speckle tracking moving from one stretch state to the next for correlation coefficient of the axial pixel displacements between these two stretch states.
Figure 22:
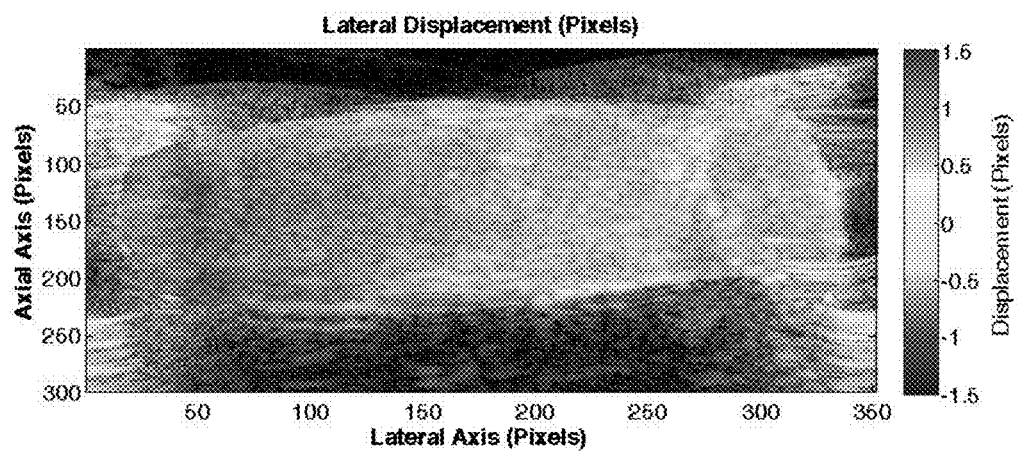
FIG. 22 illustrates a representative output from 3D speckle tracking moving from one stretch state to the next for correlation coefficient of the lateral pixel displacements between these two stretch states.
Figure 23:
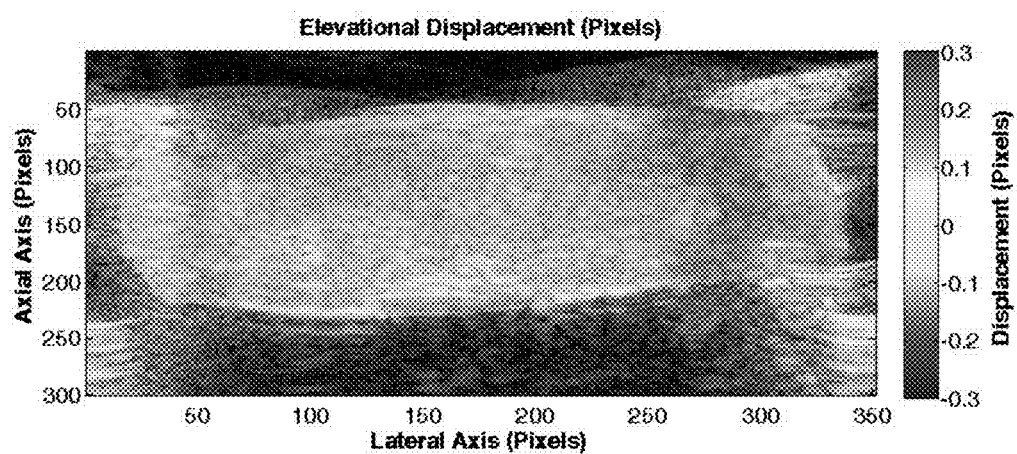
FIG. 23 illustrates a representative output from 3D speckle tracking moving from one stretch state to the next for correlation coefficient of the elevational pixel displacements between these two stretch states.

FIGS. 18 and 19 demonstrate that high density of speckles can be imaged, and that piecing multiple slices together could still produce a good continuum of speckles in the elevational direction, enabling high-fidelity correlation for 3D speckle tracking as shown in FIG. 20.

The experimental biaxial testing was performed in quasi-static condition rather than real time condition because the high frequency ultrasound transducer used was a 1D linear-array for cross-sectional 2D imaging. 3D scans were achieved through translating the transducer in the elevational axis with a linear actuator, acquiring a stack of 2D ultrasound images, and undergoing 3D reconstruction. It took a few seconds to acquire each 3D volume image, during which the sample need to be held stationary, thus requiring the quasi-static testing protocol. Alternatively, other 3D volume imaging techniques can be adapted for real-time dynamic testing.

To counter effects of viscoelastic stress relaxation, the sample was allowed to relax in the stress-free state for recovery in between stretching cycles. Further, the sample was preconditioned to peak stretch level before the test. However, stress relaxation effects were minimal, as illustrated in FIG. 17A, which showed that the peak loading condition of each quasi-static cycle (traceable with the dots in the figure) matched the loading curve of a single fully dynamic test cycle (represented by the final pre-conditioning cycle, the dark line in figure).

FIGS. 20-23 illustrate exemplary outputs from the 3DUST algorithm, which performed 3D cross-correlation between two consecutive image volumes. The correlation coefficients were generally high (>0.8 at locations where data is utilized), illustrating that the output had high fidelity. Lateral displacements show opposite ends moving away from one another, in agreement the tensile motion imposed by the biaxial tester on the sample.

Figure 24A:
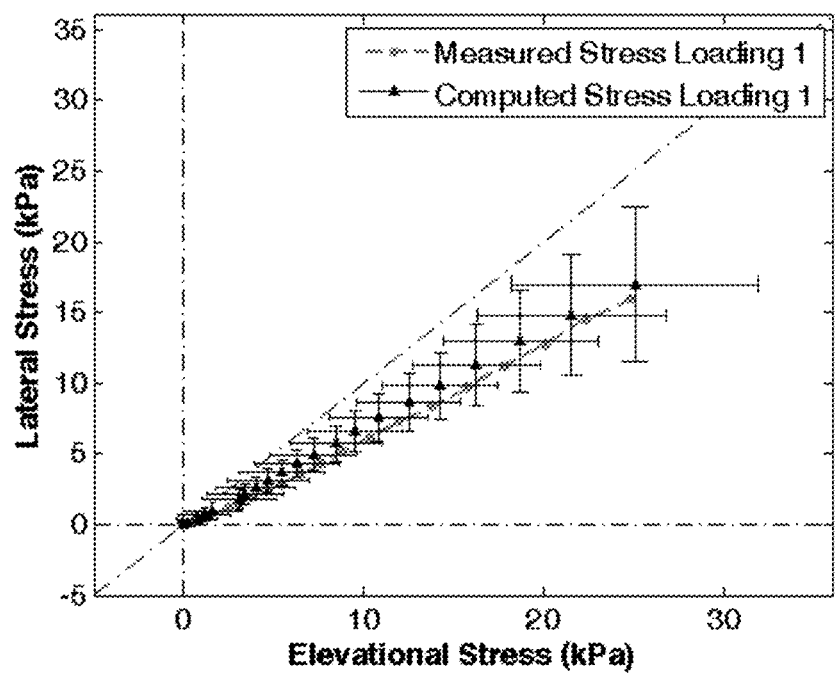
FIGS. 24A and 24B illustrate plots of measured stresses for a first loading condition, obtained by dividing measured forces by cross sectional areas (gray line), and computed stresses, obtained through the non-linear curve fitting, presented as the mean and standard deviation of stresses over all points included in the curve fitting (black line with standard deviation bars).
Figure 24B:
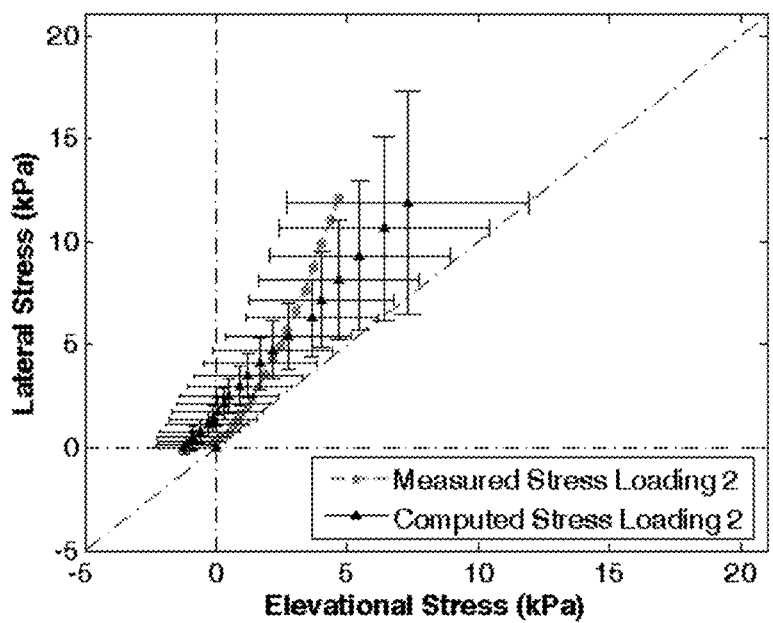

FIGS. 24A, 24B, 25A, 25B illustrate the fit between the stresses measured by the actuator and the stresses computed through the inverse computation algorithm. The computed stresses demonstrated spatial variations, as represented by the error bars. Fiber orientations were computed over a regularly spaced grid covering about half the myocardium thickness, within 4 ultrasound planes spaced 0.203 mm from one another. FIGS. 24A and 24B were plotted with the SEF in equation 1 (above), while FIGS. 25A and 25B were plotted with a different SEF:

$$W = c_1(\alpha-1)^2 + c_2(\alpha-1)^3 + c_3(I_1-3) + c_4(I_1-3)(\alpha-1) + c_5(I_1-3)^2, \quad \text{(Eqn. 3)}$$

where $c_1$-$c_5$ are the SEF coefficients.

FIGS. 24A, 24B, 25A, and 25B show that altering the form of the SEF can improve the match between the measured stress and stresses computed by the inverse computation. The goodness-of-fit parameters are displayed in the table shown in FIG. 33. FIG. 33 illustrates goodness of fit between stress tensor diagonals measured from experiments and computed using the inverse algorithm, showing that fit can be improved by altering the SEF form. $M_2^o$ is the second moments of the difference between the measured stress ($\sigma_{ii}^{mea}$) and the computed stress ($\sigma_{ii}^{comp}$); $A^o$ is the difference between measured stress and mean computed stress. Parameters were first computed for every quasi-static steps, and then averaged over all quasi-static steps before being reported.

Figure 25A:
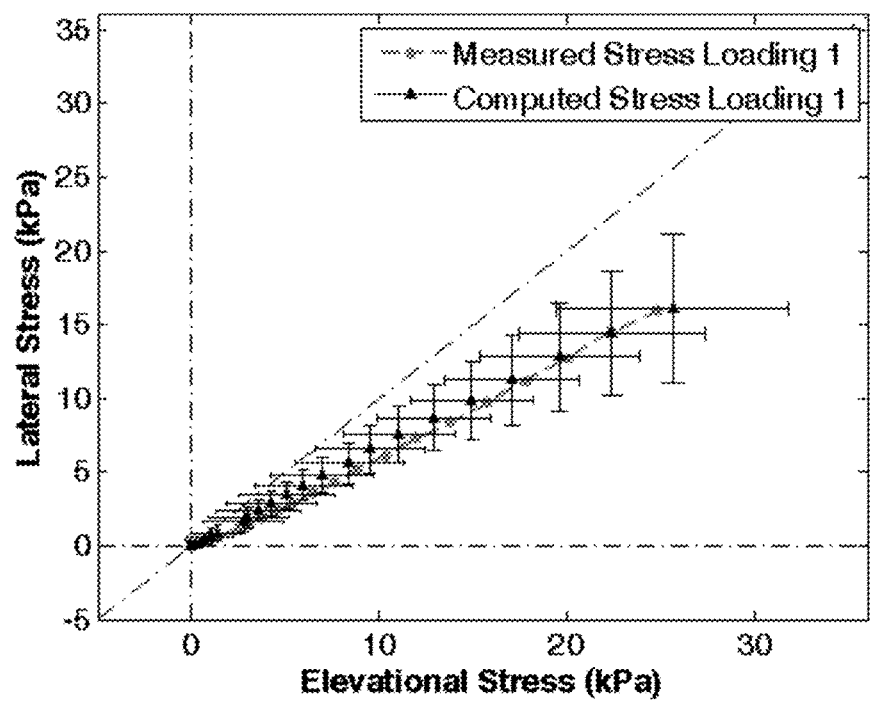
FIGS. 25A and 25B illustrate plots of measured stresses for a second loading condition, obtained by dividing measured forces by cross sectional areas (gray line and computed stresses, obtained through the non-linear curve fitting, presented as the mean and standard deviation of stresses over all points included in the curve fitting (black line with standard deviation bars).
Figure 25B:
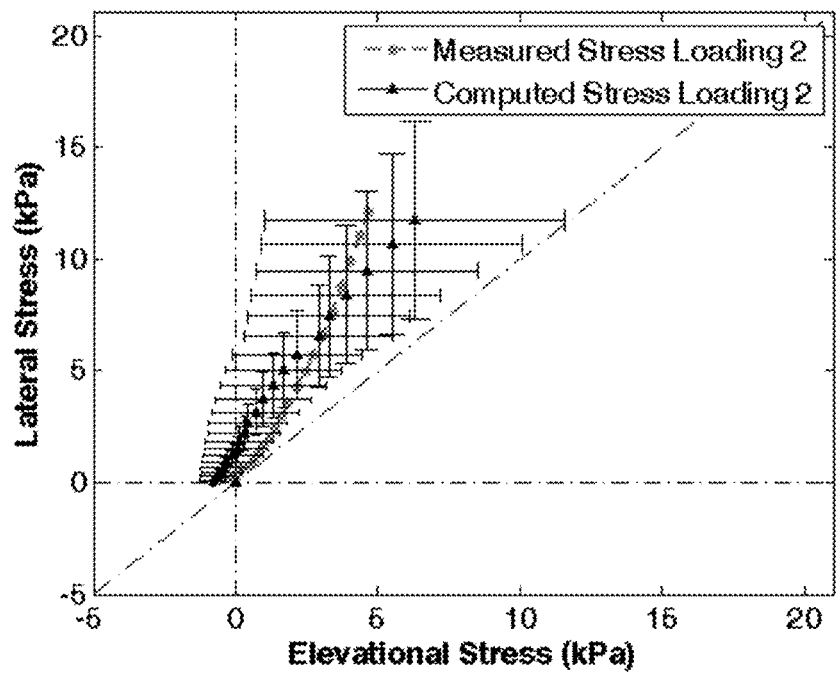

From the inverse computation results, the match between computed stresses and measured stresses can be obtained as shown in FIGS. 24A and 24B. With the current SEF (equation 1), the match in loading condition 2 was not as good. However, the match can be resolved by refining the form of the SEF, as illustrated in FIGS. 25A and 25B, which was plotted with a different SEF. Accordingly, in some embodiments, the method can comprise selecting the SEF with the most suitable form for the particular tissue being studied. FIGS. 24A, 24B, 25A, and 25B further reflected spatial variations in stresses around its mean value, which may be a result of realistic spatial variation in stresses, errors stemming from spatial variation of material stiffness, or a combination of the two.

Figure 26:
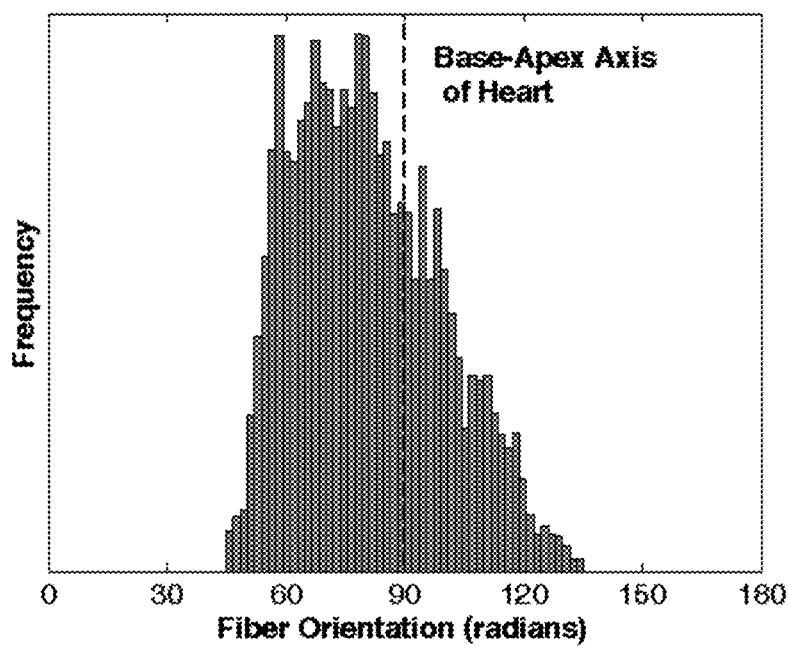
FIG. 26 illustrates a histogram of fiber orientations over all points included in the non-linear curve fit, which covered 4 planes spaced 0.203 mm apart.
Figure 27:
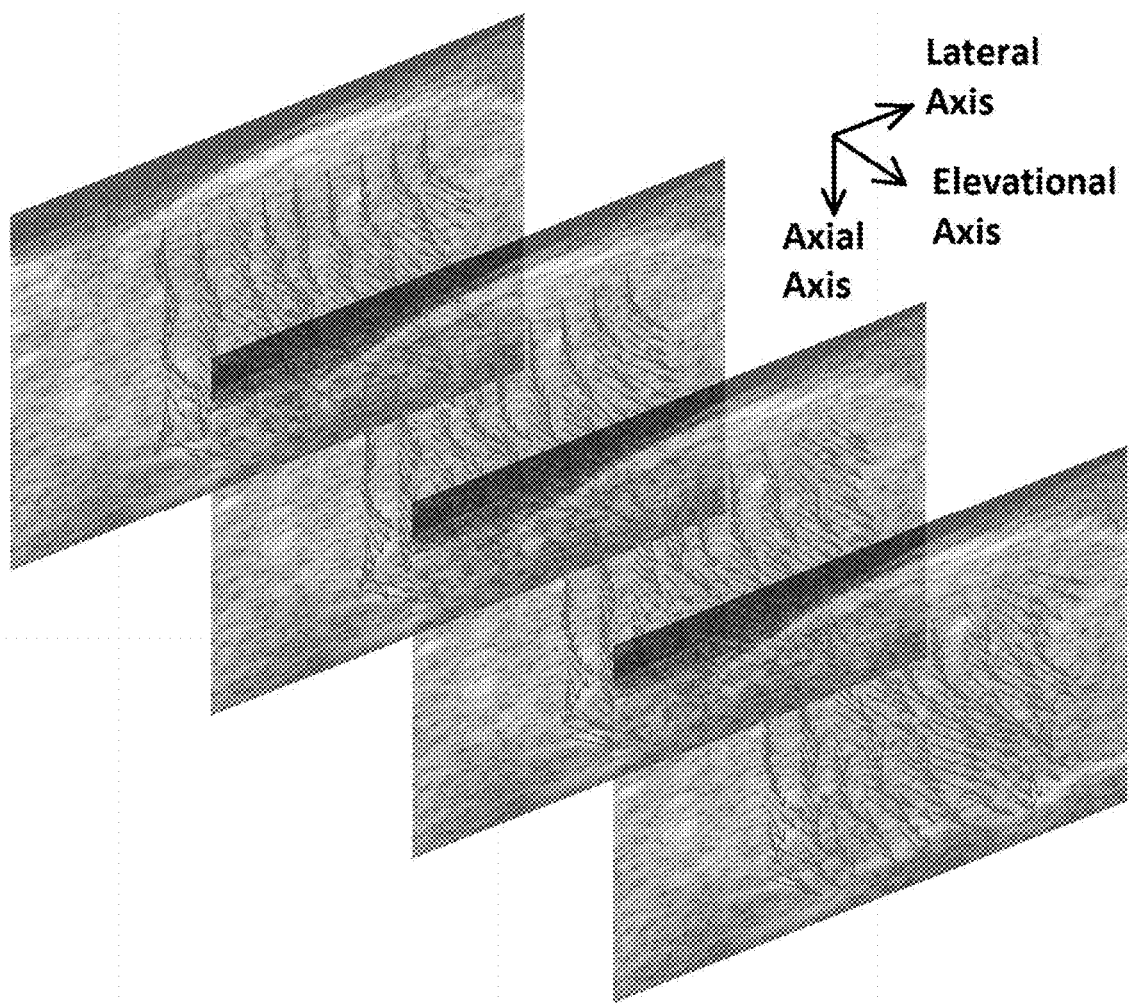
FIG. 27 illustrates a graphical rendering of the fiber orientation within 4 planes, with planes were spaced 0.203 mm apart and data points included in the non-linear curve fit, and with fiber orientation indicated by arrows.
Figure 28:
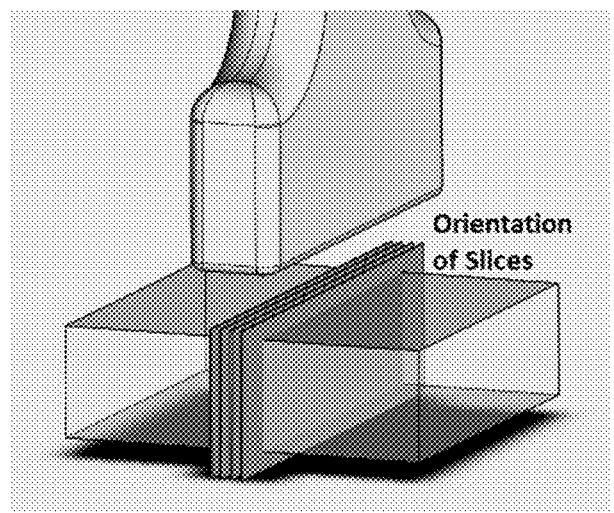
FIG. 28 illustrates the orientation of the 4 planes shown in FIG. 27 with respect to the ultrasound transducer and sample.

FIG. 26 depicts the histogram of the fiber orientation data from all 4 planes, which presented as a slightly skewed bell curve. The spatial variation of fiber orientation is rendered in FIG. 27. The 4 planes were spaced 0.203 mm apart. Note that all arrows are plotted with the same lengths, but some arrows appear shorter due to the orientation of the arrow. These arrows are plotted at ⅛ of the actual data resolution. In FIG. 28, the orientation of the 4 planes shown in FIG. 27 with respect to the ultrasound transducer and sample is illustrated. Fiber orientation was computed as 80.7±18.4 degrees, the mean was approximately 10 degrees from the base-apex axis of the heart. SEF coefficients, averaged across the 4 planes, are shown in the table of FIG. 34. Variations between different planes were relatively small, having standard deviations of less than 15% the mean value.

FIG. 26 shows that spatially varying fiber orientations could be inverse-computed using our method, while FIGS. 29 and 30 (discussed below) provided validation for the computed values. The variation of fiber orientation from the outer layers towards the inner layers over the range of approximately 2 mm thickness of myocardium or about ⅔ of the full thickness, was about 57 degrees, translating to 86 degrees over the entire sample thickness. This result had a good agreement with fiber orientations computed through histology when plotted as a function of axial coordinates.

Figure 29A:
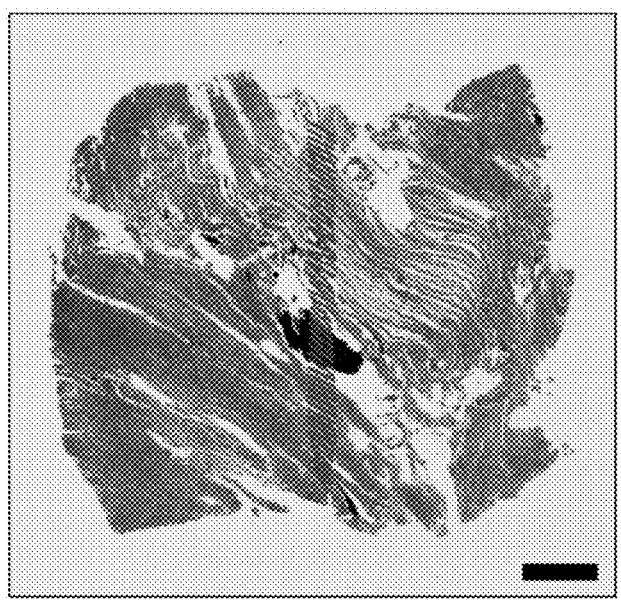
FIG. 29A illustrates Masson's trichrome stains of rat left ventricular myocardium samples in the Lateral-Elevational plane, with the sample taken from near the epicardium.
Figure 29B:
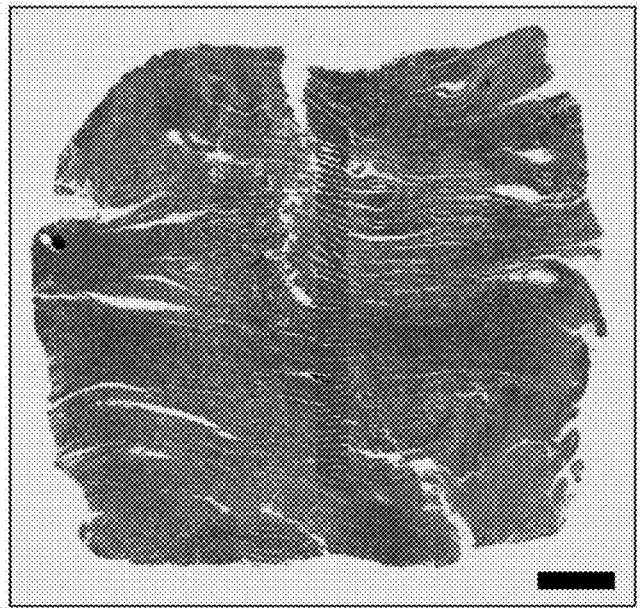
FIG. 29B illustrates Masson's trichrome stains of rat left ventricular myocardium samples in the Lateral-Elevational plane, with the sample taken from the middle myocardium layer (b), and near the endocardium (c).
Figure 29C:
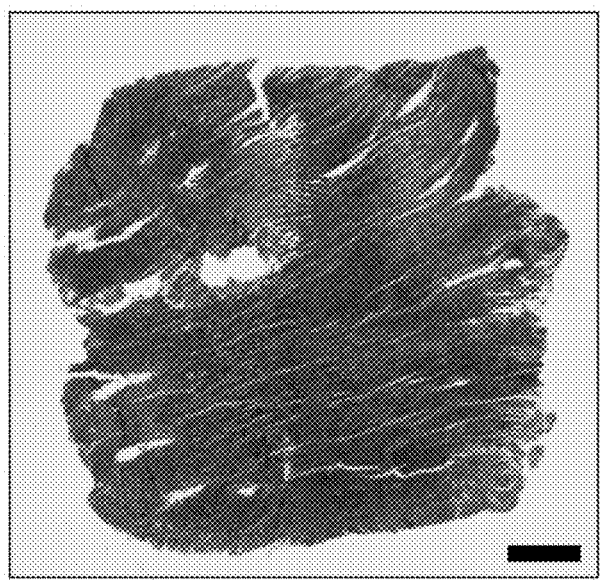
FIG. 29C illustrates Masson's trichrome stains of rat left ventricular myocardium samples in the Lateral-Elevational plane, with the sample taken from near the endocardium.
Figure 29D:
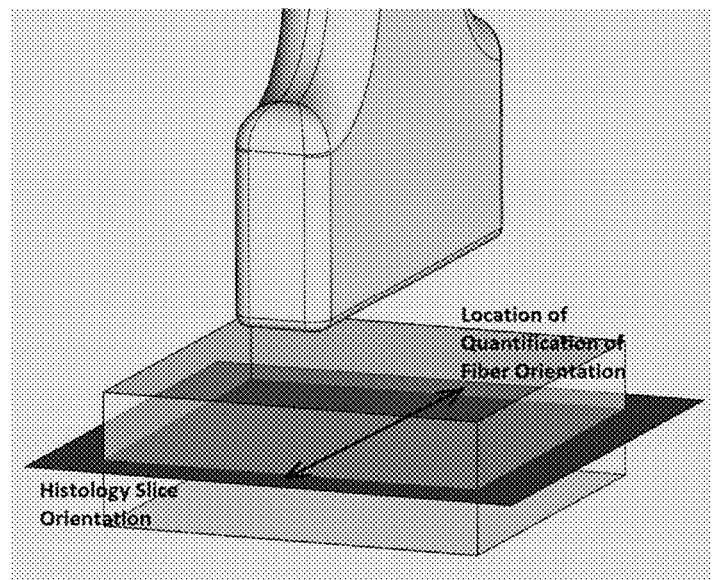
FIG. 29D illustrates a schematic of the orientation of these histology samples with respect to the ultrasound-biaxial mechanical testing.

Three representative histological images are presented in FIGS. 29A-29C. These figures illustrate Masson's trichrome stains of the rat left ventricular myocardium samples in the Lateral-Elevational plane. Three samples at different tissue depths are shown: near the epicardium (FIG. 29A), in the middle myocardium layer (FIG. 29B), and near the endocardium (FIG. 29C). Fiber orientations were computed based on these images using 2D Fourier analysis, and were plotted as solid lines at approximate locations where analysis using our ultrasound-biaxial method was performed. The scale bar indicates 100 microns. FIG. 29D illustrates the location of quantification of fiber orientation and histology slice orientation, and shows a schematic of the orientation of these histology samples with respect to the ultrasound-biaxial mechanical testing.

A gradual change of fiber orientation from the outer to inner layers was clearly observable. The fiber orientations obtained through Fourier analysis of histological images were plotted as arrows on these images, along the lateral axis. FIG. 29D illustrates the location of quantification of fiber orientation and histology slice orientation.

Figure 30:
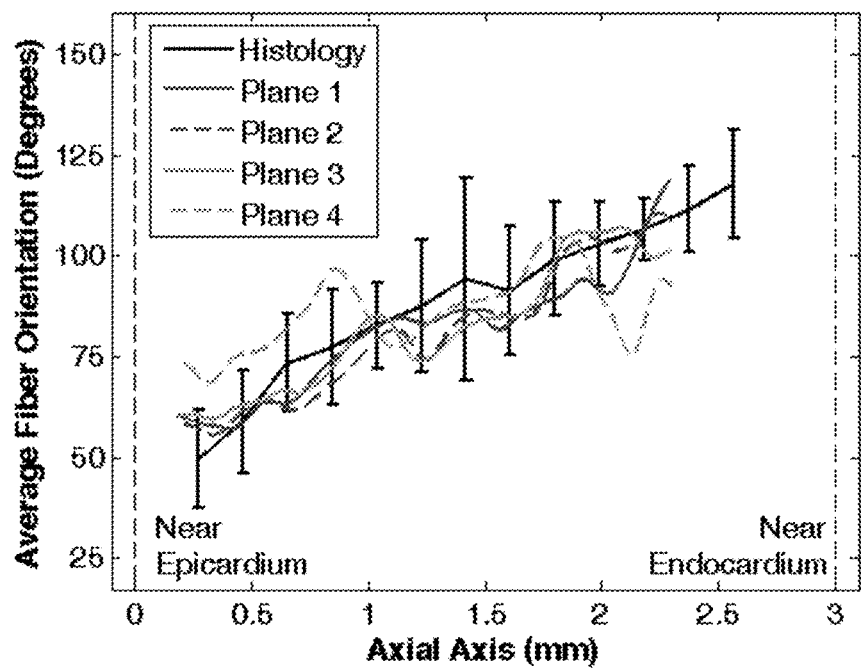
FIG. 30 illustrates a plot of fiber orientation versus tissue depth (axial coordinates) near the central region of a sample, shown for ⅔ of the total thickness of the sample, with both data computed using histology (black line) and data computed using ultrasound-biaxial mechanical testing (gray lines).

FIG. 30 illustrates plot of fiber orientation versus tissue depth (axial coordinates) near the central region of the sample, shown for ⅔ of the total thickness of the sample. Both data computed using histology (black line) and data computed using ultrasound-biaxial mechanical testing (gray lines) are shown. With the latter, each gray line corresponds to one of the four planes analyzed. The approximate outer (epicardium) and inner (endocardium) boundaries of the sample are indicated as dotted lines on the left and right edge of the plot.

In FIG. 30, fiber orientations at the same axial coordinate were averaged, and were plotted versus axial coordinates (depth of sample). Data obtained from histology showed a generally good agreement with data obtained from the inverse computation from the biaxial-ultrasound experiment. This provides qualitative validation of our inverse method. Generally, a gradual increase in the fiber angle of approximately 57 degrees is observed from the outer layers to the inner layers over the half-thickness of the myocardium investigated.

Although the biaxial mechanical testing in the examples could distribute stresses in the elevational and lateral direction at the edges of the sample attached to the hooks, there was no mechanism in the experimental setup to distribute stresses along the axial direction at these edges of the sample. Alternative mounting arrangements can be provided to achieve an ideal distribution of stresses in the axial direction at the edge of the sample, for example, compressing the sample in the axial direction with uniaxial strains.

The systems and methods described herein provide mechanical testing of biological samples that combines 3D-UST with a traditional biaxial mechanical testing. These techniques improve on conventional testing techniques in which tissue deformation measurements are achieved by superficial optical tracking. The systems and methods described herein can provide 3D ultrasound for volumetric imaging, which provides a complete set of strain tensor over entire 3D volumes. This additional measurement capability allows for the computation of tissue fiber orientation.

In some embodiments, the systems and methods provided herein permit inverse reconstruction algorithm from ultrasound radiofrequency data and stress-strain data. These systems and methods can be applied to any soft tissue mechanical measurements, providing information about both mechanical properties and fiber orientation, and the relationships between them.

The examples described herein are exemplary. Consistent with this disclosure, ultrasound elasticity imaging and mechanical testing can be combined in other systems. For example, ultrasound elasticity imaging can also be combined with other mechanical testing methods such as vascular pressure-diameter and force-length mechanical testing, three point bending tests for heart valves, pure shear tests for the liver, and simple uni-axial compression tests. These implementations can provide additional information about the samples, such as elucidation of fiber orientation details to explain characteristics of 3D vascular wall pre-stresses.

Further, in many cases, biomaterial implants can experience non-homogeneous tissue invasion or growth at different layers of the implant. Because the systems and methods described herein can assess spatially varying mechanical characteristics, additional benefits can be achieved. For example, by approximating in vivo stresses (such as using hoop stress theory or in vivo force measuring devices), the systems and methods can be used in in vivo evaluation of mechanical properties and fiber orientations.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A system for determining constitutive mechanical relations and fiber orientation of tissue samples, the system comprising:
    a biaxial tester configured to apply a force to a sample to stretch the sample along a plurality of axes;
    an ultrasound device configured to move relative to the tissue sample; and
    a computing system a processor and a data storage device comprising a non-transitory computer-readable medium having instructions stored therein that, when executed by the processor, cause the processor to:
        direct the ultrasound device at the sample and obtain 3D ultrasound images of the stretched sample along the plurality of axes to determine an amount of strain on the sample;
        determine a fiber orientation of a volume of the sample based, at least in part, on the determined amount of strain on the sample while stretched along the plurality of axes from displacements within the volume calculated from the obtained 3D ultrasound images; and
        display a visual representation of the determined fiber orientation of the volume.

2. The system of claim 1, wherein the biaxial tester comprises a tissue holding device that is moveable via a motorized unit to vary the amount of force applied to the sample.

3. The system of claim 1, wherein the ultrasound device comprises a high-frequency 3D ultrasound speckle tracking device.

4. The system of claim 1, wherein the ultrasound device is coupled to the biaxial tester and suspended over a sample-receiving area of the biaxial tester.

5. The system of claim 1, wherein the biaxial tester comprises a plurality of sample-securing members located around a sample-receiving area to secure the sample at a plurality of locations.

6. The system of claim 5, wherein the biaxial tester comprises a plurality of pulleys to distribute a load applied to the sample.

7. The system of claim 1, wherein the biaxial tester is configured to apply a periodically increasing load to the sample, and the ultrasound device is configured to image the sample at a substantially peak stretch amount during each period.

8. The system of claim 1, wherein the ultrasound device is coupled to the biaxial tester.

* * * * *

UNITED STATES PATENT AND TRADEMARK OFFICE
CERTIFICATE OF CORRECTION

PATENT NO. : 11,808,754 B2
APPLICATION NO. : 16/727879
DATED : November 7, 2023
INVENTOR(S) : Kim et al.

Page 1 of 1

It is certified that error appears in the above-identified patent and that said Letters Patent is hereby corrected as shown below:

In the Claims

Column 14, Lines 42-44, Claim 1 "a computing system a processor and a data storage device comprising a non-transitory computer-readable medium having instructions stored therein" should read -- a computing system having a processor and a data storage device comprising a non-transitory computer-readable medium having instructions stored therein --

Signed and Sealed this
Thirtieth Day of April, 2024

Katherine Kelly Vidal
*Director of the United States Patent and Trademark Office*